United States Patent [19]

Crounse et al.

[11] 4,075,224

[45] Feb. 21, 1978

[54] 3,5-BIS(INDOLYL)-5-(INDOLYL)-2(5H)-FURANONES

[75] Inventors: Nathan Norman Crounse, Cincinnati; Paul Joseph Schmidt, Sharonville, both of Ohio

[73] Assignee: Sterling Drug Inc., New York, N.Y.

[21] Appl. No.: 651,607

[22] Filed: Jan. 22, 1976

[51] Int. Cl.$^2$ .................. C07D 209/18; C07D 209/20
[52] U.S. Cl. .......................... 260/326.14 R; 106/14.5; 106/21; 106/22; 260/326.13 R; 427/151
[58] Field of Search ............................ 260/326.14 R

[56] References Cited

U.S. PATENT DOCUMENTS

| 3,509,174 | 4/1970 | Lin | 260/326.14 R |
| 3,812,146 | 5/1974 | Farber et al. | 260/326.14 R |

*Primary Examiner*—Dolph H. Torrence
*Attorney, Agent, or Firm*—Lynn T. Fletcher; B. Woodrow Wyatt

[57] ABSTRACT

Mono-, bis- and tris-indolyl-substituted furanones useful as color formers, particularly in carbonless duplicating and thermal marking systems, which are prepared respectively by: the interaction of an indole with mucochloric acid; the interaction of an indole with a 4-mono(indolyl)-substituted 4-oxo-2-butenoic acid; and by the interaction of an indole with a 2,4-bis(indolyl)-substituted 4-oxobutanoic acid or with a 3,5-bis(indolyl)-substituted furanone.

20 Claims, No Drawings

3,5-BIS (INDOLYL)-5-(INDOLYL)-2(5H)-FURANONES

BACKGROUND OF THE INVENTION a. Field of the Invention

This invention relates to mono-, bis- and tris-(1and/or 2 substituted-3-indolyl)-substituted -2-furanones useful as color precursors, particularly in the art of carbonless duplicating as, for example, in pressure-sensitive systems and in thermal marking systems; to substituted butanoic and butenoic acids useful as intermediates to these furanones; and to processes for preparing said indolyl-substituted furanones, butanoic acids and butenoic acids.

b. Description of the Prior Art

Several classes of organic compounds of widely diverse structural types are known to be useful as colorless precursors to dyestuffs. Said precursors have applications in the art of dyeing and coloring, for example, in the dyeing and printing of textiles and in the art of carbonless duplicating. Among the more important classes useful in the carbonless duplicating art, there may be named phenothiazines, for example, benzoyl leuco methylene blue; phthalides, for example, crystal violet lactone; fluorans, for example, 2'-anilino-6'-diethylaminofluoran and 2'-dibenzylamino-6'-diethylaminofluoran; and various other types of colorless precursors currently employed in commercially accepted carbonless copy systems. Typical of the many such systems taught in the prior art are those described in U.S. Pat. Nos. 2,712,507, 2,800,457 and 3,041,289. However, to the present time, there appears to be no evidence that the indolyl-substituted furanones constituting the subject matter of this invention have been employed as color formers, particularly in carbonless duplicating systems or in thermal marking systems. Representative of thermal marking systems disclosed in the prior art are those described in U.S. Pat. Nos. 3,539,375 and 3,895,173.

Rees and Sabet in the Journal of the Chemical Society, 687–691 (1965) [Chemical Abstracts 62: 6475h (1965)] describe the preparation and physical characteristics of 3,4-dichloro-5-(3-indolyl)-2(5H)-furanone and 3,4-dichloro-5-(2-methyl-3-indolyl)-2(5H)-furanone without giving any indication of their utility. Barrett, Beer, Dodd and Robertson in the Journal of the Chemical Society, 4810–4813 (1957) [Chemical Abstracts 52: 100053e (1958)] describe the preparation and the physical characteristics of 5-(1-acetyl-5-substituted-3-indolyl)-2-(3H)-furanones. The compounds are described as intermediates in a structural confirmation synthesis. We have now discovered that the compounds described by Rees and Sabet are readily converted to colored substances on thermal exposure. This property makes them useful for incorporation into thermal marking systems such as are used in recording and in duplicating systems.

Diels and Alder in Annalen Der Chemie 490: 277–294 (1931) [Chemical Abstracts 26: 438 (1932)] describe the preparation and physical characteristics of 2,4-bis(2-methyl-3-indolyl)-4-oxobutanoic acid and 2,4-bis(1,2-dimethyl-3-indolyl)-4-oxobutanoic acid. There is no indication of the utility of the compounds given in the reference. Jackson and Naidoo in Journal Chemical Society, Perkins Transactions II; (5): 548–551 (1973) [Chemical Abstracts 78: 12439h (1973)] describe the preparation and physical characteristics of 4-(2-methyl-3-indolyl)-4-oxobutanoic acid as a chemical intermediate for the preparation of the corresponding methyl ester for which no utility is given.

SUMMARY OF THE INVENTION

In one of its composition of matter aspects, the invention relates to certain 3-Z-4-$Z_1$-5-$Z_2$-5-(1-R-2-$R_1$-5/6-Y-3-indolyl)-2(5H)-furanones which are final products useful as colorless precursors in carbonless duplicating systems.

In a second composition of matter aspect, the invention relates to certain 3,5-bis(1-R-2-$R_1$-5/6-Y-3-indolyl)-2-(3H)-furanones which, in addition to having the same utility as the final products, are useful as intermediates for the preparation of other final products of the invention.

In a third composition of matter aspect, the invention relates to certain 2,4-bis(1-R-2-$R_1$-5/6-Y-3-indolyl)-4-oxobutanoic acids which are useful as intermediates for the preparation of the final products of the invention.

In a fourth composition of matter aspect, the invention relates to certain 4-(1-R-2-$R_1$-5/6-Y-3-indolyl)-2,3-dichloro-4-oxo-2-butenoic acids which are useful as intermediates for the preparation of the final products of the invention.

In one of its process aspects, the invention relates to a process for preparing the 3-Z-4-$Z_1$-5-$Z_2$-5-(1-R-2-$R_1$-5/6-Y-3-indolyl)-2(5H)-furanones in which Z is 1-R-2-$R_1$-5/6-Y-3-indolyl and $Z_2$ is 1-$R_2$-2-$R_3$-5/6-$Y_1$-3-indolyl which comprises interacting the appropriate 2,4-bis(1-R-2-$R_1$-5/6-Y-3-indolyl)-4-oxobutanoic acid with an appropriate 1-$R_2$-2-$R_3$-5/6-$Y_1$-indole.

In a second of its process aspects, the invention relates to a process for preparing the 3,5-bis(1-R-2-$R_1$-5/6-Y-3-indolyl)-2(3H)-furanones which comprises the ring closing cyclization of an appropriate 2,4-bis(1-R-2-$R_1$-5/6-Y-3-indolyl)-4-oxobutanoic acid.

In a third of its process aspects, the invention relates to a process for preparing the 3-Z-4-$Z_1$-5-$Z_2$-5-(1-R-2-$R_1$-5/6-Y-3-indolyl)-2(5H)-furanones in which Z is 1-R-2-$R_1$-5/6-Y-3-indolyl and $Z_2$ is 1-$R_2$-2-$R_3$-5/6-$Y_1$-3-indolyl which comprises interacting the appropriate 3,5-bis(1-R-2-$R_1$-5/6-Y-3-indolyl)-2(3H)-furanone with an appropriate 1-$R_2$-2-$R_3$-5/6-$Y_1$-indole.

In the fourth of its process aspects, the invention relates to a process for the rearrangement of the double bond in the furanone ring of 3,5-bis(1-R-2-$R_1$-5/6-Y-3-indolyl)-2(3H)-furanones to obtain 3,5-bis(1-R-2-$R_1$-5/6-Y-3-indolyl)-2(5H)-furanones.

In the fifth of its process aspects, the invention relates to a process for preparing the 5-(1-R-2-$R_1$-5/6-Y-indolyl)-5-(1-$R_2$-2-$R_3$-5/6-$Y_1$-3-indolyl)-3,4-dichloro-2(5H)-furanones which comprises interacting the appropriate 4-(1-R-2-$R_1$-5/6-Y-3-indolyl)-2,3-dichloro-4-oxo-2-butenoic acid with an appropriate 1-$R_2$-2-$R_3$-5/6-$Y_1$-indole.

In the sixth of its process aspects, the invention relates to a process for preparing 4-(1-R-2-$R_1$-5/6-Y-3-indolyl)-2,3-dichloro-4-oxo-2-butenoic acids which comprises interacting dichloromaleic anhydride with an appropriate 1-R-2-$R_1$-5/6-Y-indole.

In the seventh of its process aspects, the invention relates to a process for preparing 3,5-bis(1-R-2-$R_1$-5/6-Y-3-indolyl)-5-(1-$R_2$-2-$R_3$-5/6-$Y_1$-3-indolyl)-2(5H)-furanones in which R=$R_2$, $R_1$=$R_3$ and Y=$Y_1$ which comprises interacting maleic anhydride with the appropriate substituted 1-R-2-$R_1$-5/6-Y-indole.

In still another aspect, the invention relates to pressure-sensitive carbonless duplicating systems and/or to thermal marking systems which contain any of the above-mentioned -3-Z-4-$Z_1$-5-$Z_2$-5-(1-R-2-$R_1$-5/6-Y-3-indolyl)-2(5H)-furanones or 3,5-bis(1-R-2-$R_1$-5/6-Y-3-indolyl)-2(3H)-furanones represented by Formulas I and II, respectively.

DETAILED DESCRIPTION INCLUSIVE OF THE PREFERRED EMBODIMENTS

More specifically, this invention, in one of its composition of matter aspects relating to the final products, resides in the novel indolyl-substituted 2-furanones, which are particularly useful as colorless precursors in the art of carbonless duplicating, and which are selected from the group consisting of 3-Z-4-$Z_1$-5-$Z_2$-5-(1-R-2-$R_1$-5/6-Y-3-indolyl)-2(5H)-furanones having the formula

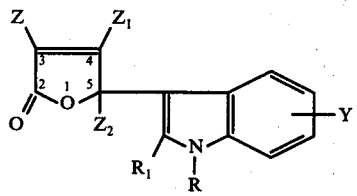

Formula I and 3,5-bis(1-R-2-$R_1$-5/6-Y-3-indolyl)-2(3H)-furanones having the formula

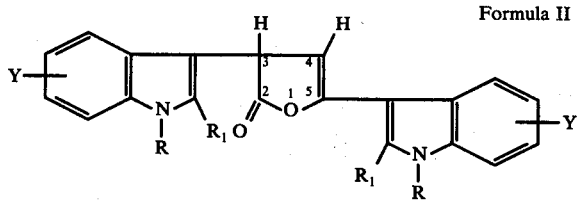

Formula II wherein Z when $Z_1$ is chlorine and at least one of $Z_2$ and R is other than hydrogen, represents chlorine, or when $Z_1$ is hydrogen, represents a monovalent 1-R-2-$R_1$-5/6-Y-3-indolyl moiety of the formula

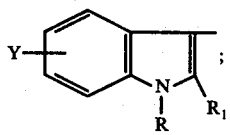

$Z_1$ represents hydrogen or when Z is chlorine and at least one of $Z_2$ and R is other than hydrogen, represents chlorine; $Z_2$ represents hydrogen or a monovalent 1-$R_2$-2-$R_3$-5/6-$Y_1$-3-indolyl moiety of the formula

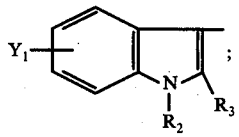

R and $R_2$ represent hydrogen, non-tertiary alkyl of one to eight carbon atoms, alkenyl of two to four carbon atoms, benzyl or benzyl substituted in the benzene ring by one or two of halo or alkyl of one to three carbon atoms; $R_1$ and $R_3$ represent hydrogen, alkyl of one to three carbon atoms or phenyl; and Y and $Y_1$ represent one or two of hydrogen, alkyl of one to three carbon atoms, alkoxy of one to three carbon atoms, halo or nitro.

In addition to being final products, the 3,5-bis(1-R-2-$R_1$-5/6-Y-3-indolyl)-2(3H)-furanones of Formula II also form one of the composition of matter aspects of this invention relating to intermediates.

In a first particular embodiment in accordance with its final product composition of matter aspect, the invention sought to be patented resides in the novel 3,5-bis(1-R-2-$R_1$-5/6-Y-3-indolyl)-5-(1-$R_2$-2-$R_3$-5/6-$Y_1$-3-indolyl)-2(5H)-furanones of Formula I wherein Z is 1-R-2-$R_1$-5/6-Y-3-indolyl; $Z_1$ is hydrogen; and $Z_2$ is 1-$R_2$-2-$R_3$-5/6-$Y_1$-3-indolyl. Preferred compounds within the ambit of this particular embodiment are of the formula

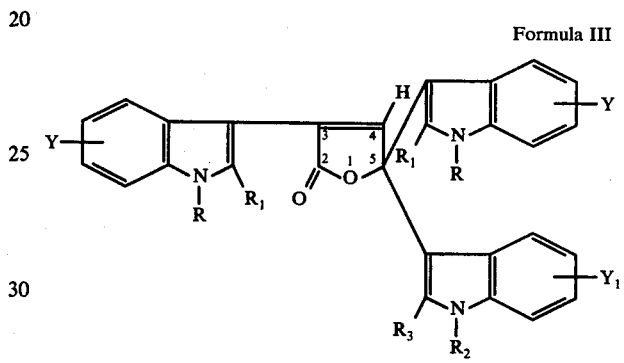

Formula III wherein R, $R_1$, $R_2$, $R_3$, Y and $Y_1$ have the same respective meanings given in relation to Formula I.

In a second particular embodiment in accordance with its final product composition of matter aspect, the invention sought to be patented resides in the novel 3,5-bis(1-R-2-$R_1$-5/6-Y-3-indolyl)-2(5H)-furanones of Formulas I wherein Z is 1-R-2-$R_1$-5/6-Y-3-indolyl; and $Z_1$ and $Z_2$ are each hydrogen. Preferred compounds within the ambit of this particular embodiment are of the formula

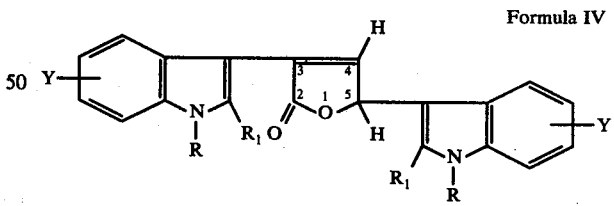

Formula IV wherein R, $R_1$ and Y have the same respective meanings given in relation to Formula I.

In a third particular embodiment in accordance with its final product composition of matter aspect, the invention sought to be patented resides in the novel 5-(1-R-2-$R_1$-5/6-Y-3-indolyl)-5-(1-$R_2$-2-$R_3$-5/6-$Y_1$-3-indolyl)-3,4-dichloro-2(5H)-furanones of Formula I wherein Z and $Z_1$ are each chlorine; and $Z_2$ is 1-$R_2$-2-$R_3$-5/6-$Y_1$-3-indolyl. Preferred compounds within the ambit of this particular embodiment are of the formula

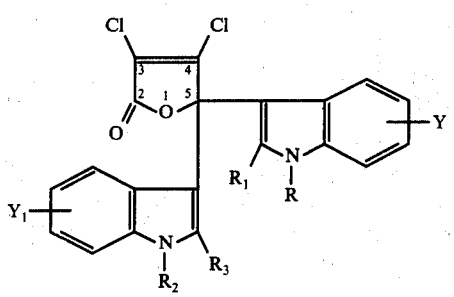

Formula V wherein R, $R_1$, $R_2$, $R_3$, Y and $Y_1$ have the same respective meanings given in relation to Formula I.

In a fourth particular embodiment in accordance with its final product composition of matter aspect, the invention sought to be patented resides in the novel 5-(1-R-2-$R_1$-5/6-Y-3-indolyl)-3,4-dichloro-2(5H)-furanones of Formula I wherein Z and $Z_1$ are each chlorine; and $Z_2$ is hydrogen. Preferred compounds within the ambit of this particular embodiment are of the formula

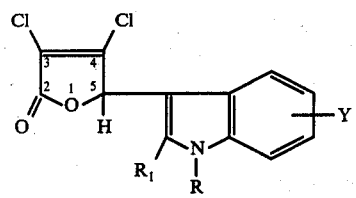

Formula VI wherein R, $R_1$ and Y have the same respective meanings given in relation to Formula I.

In a fifth particular embodiment in accordance with its final product composition of matter aspect, the invention sought to be patented resides in the novel 3,5-bis(1-R-2-$R_1$-5/6-Y-3-indolyl)-2(3H)-furanones of Formula II wherein R, $R_1$ and Y each have the same respective meanings indicated in relation to Formula II.

This invention, in a second of its composition of matter aspects, relating to intermediates, resides in the novel 2,4-bis(1-R-2-$R_1$-5/6-Y-3-indolyl)-4-oxobutanoic acids which are useful as intermediates to the final products and having the formula

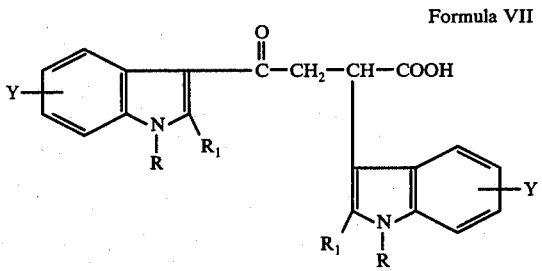

Formula VII wherein R represents hydrogen, non-tertiary alkyl of one to eight carbon atoms, alkenyl of two to four carbon atoms, benzyl or benzyl substituted in the benzene ring by one or two of halo or alkyl of one to three carbon atoms; $R_1$ represents hydrogen, alkyl of one to three carbon atoms or phenyl; Y represents one or two of hydrogen, alkyl of one to three carbon atoms, alkoxy of one to three carbon atoms, halo or nitro; and with the proviso that R cannot be hydrogen or methyl when $R_1$ is methyl and Y is hydrogen.

This invention, in a third of its composition of matter aspects, relating to intermediates, resides in the novel 4-(1-R-2-$R_1$-5/6-Y-3-indolyl)-2,3-dichloro-4-oxo-2-butenoic acids, which are useful as intermediates to the final product and having the formula

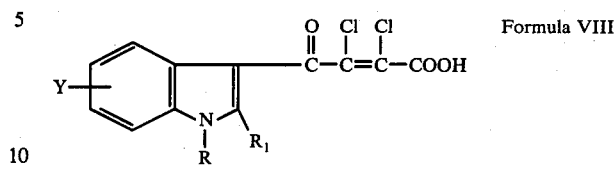

Formula VIII wherein R represents hydrogen, non-tertiary alkyl of one to eight carbon atoms, alkenyl of two to four carbon atoms, benzyl or benzyl substituted in the benzene ring by one or two of halo or alkyl of one to three carbon atoms; $R_1$ represents hydrogen, alkyl of one to three carbon atoms or phenyl; and Y represents one or two hydrogen, alkyl of one to three carbon atoms, alkoxy of one to three carbon atoms, halo or nitro.

In one of its process aspects, the invention sought to be patented resides in the process for the preparation of the novel 3,5-bis(1-R-2-$R_1$-5/6-Y-3-indolyl)-5-(1-$R_2$-2-$R_3$-5/6-$Y_1$-3-indolyl)-2(5H)-furanones of Formula III and also represented by Formula I in which Z is 1-R-2-$R_1$-5/6-Y -3-indolyl; $Z_1$ is hydrogen; and $Z_2$ is 1-$R_2$-2-$R_3$-5/6-$Y_1$-3-indolyl which comprises interacting an appropriate 2,4-bis(1-R-2-$R_1$-5/6-Y-3-indolyl)-4-oxobutanoic acid with approximately one molecular proportion of an appropriate 1-$R_2$-2-$R_3$-5/6-$Y_1$-indole wherein R, $R_1$, $R_2$, $R_3$, Y and $Y_1$ have the same respective meanings indicated in Formula III.

In a second process aspect, the invention sought to be patented resides in the process for the preparation of the novel 3,5-bis(1-R-2-$R_1$-5/6-Y-3-indolyl)-2(3H)-furanones represented by Formula II which comprises the ring closing cyclization of an appropriate 2,4-bis(1-R-2-$R_1$-5/6-Y-3-indolyl)-4-oxobutanoic acid of Formula VII wherein R, $R_1$ and Y have the same respective meanings indicated in Formula VII.

In a third process aspect, the invention sought to be patented resides in the process for the preparation of the novel 3,5-bis(1-R-2-$R_1$-5/6-Y-3-indolyl)-5-(1-$R_2$-2-$R_3$-5/6-$Y_1$-3-indolyl)-2(5H)-furanones of Formula III and also represented by Formula I in which Z is 1-R-2-$R_1$-5/6-Y-3-indolyl and $Z_2$ is 1-$R_2$-2-$R_3$-5/6-$Y_1$-3-indolyl which comprises interacting the appropriate 3,5-bis(1-R-2-$R_1$-5/6-Y-3-indolyl)-2(3H)-furanone with approximately one molecular proportion of an appropriate 1-$R_2$-2-$R_3$-5/6-$Y_1$-indole wherein R, $R_1$, $R_2$, $R_3$, Y and $Y_1$ have the same respective meanings given in relation to Formula III.

In a fourth process aspect, the invention sought to be patented resides in the process for the preparation of the novel 3,5-bis(1-R-2-$R_1$-5/6-Y-3-indolyl)-2(5H)-furanones represented by Formula IV by the rearrangement of the double bond in the furanone ring of 3,5-bis(1-R-2-$R_1$-5/6-Y-3-indolyl)-2(3H)-furanones wherein R, $R_1$ and Y have the same respective meanings indicated in Formula IV.

In a fifth process aspect, the invention sought to be patented resides in the process for the preparation of the novel 5-(1-R-2-$R_1$-5/6-Y-3-indolyl)-5-(1-$R_2$-2-$R_3$-5/6-$Y_1$-3-indolyl)-3,4-dichloro-2(5H)-furanones represented by Formula V which comprises interacting an appropriate 4-(1-R-2-$R_1$-5/6-Y-3-indolyl)-2,3-dichloro-4-oxo-2-butenoic acid with approximately one molecular proportion of an appropriate 1-$R_2$-2-$R_3$-5/6-$Y_1$-indole wherein R, $R_1$, $R_2$, $R_3$, Y and $Y_1$ have the same respective meanings indicated in Formula V.

In a sixth process aspect, the invention sought to be patented resides in the process for the preparation of the novel 4-(1-R-2-$R_1$-5/6-Y-3-indolyl)-2,3-dichloro-4-oxo-2-butenoic acids represented by Formula VIII which comprises interacting an appropriate 1-R-2-$R_1$-5/6-Y-indole with approximately one molecular proportion of dichloromaleic anhydride wherein R, $R_1$ and Y have the same respective meanings indicated in Formula VIII.

In a seventh process aspect, the invention sought to be patented resides in the process for the preparation of the novel 3,5-bis(1-R-2-$R_1$-5/6-Y-3-indolyl)-5-(1-$R_2$-2-$R_3$-5/6-$Y_1$-3-indolyl)-2(5H)-furanones represented by Formula III which comprises interacting maleic anhydride with approximately one to approximately three molecular proportions of an appropriate 1-R-2-$R_1$-5/6-Y-indole wherein R=$R_2$, $R_1$=$R_3$ and Y=$Y_1$ and have the same respective meanings indicated in Formula III.

As used herein, the term "non-tertiary alkyl of one to eight carbon atoms" means saturated monovalent aliphatic radicals, including branched chain radicals, for example, methyl, ethyl, propyl, isopropyl, butyl, isobutyl, amyl, 1-methylbutyl, 3-methylbutyl, hexyl, isohexyl, heptyl, isoheptyl, octyl, isooctyl and 2-ethylhexyl.

As used herein, the term "alkenyl of two to four carbon atoms" means a monovalent aliphatic radical possessing a single double bond, for example, ethenyl (or vinyl), 2-propenyl (or allyl), 1-methylethenyl (or isopropenyl), 2-methyl-2-propenyl, 2-methyl-1-propenyl, 2-butenyl and 3-butenyl.

When the terms "alkyl of one to three carbon atoms" and "alkoxy of one to three carbon atoms" are used herein, there is meant saturated, acyclic groups which may be straight or branched as exemplified by methyl, ethyl, propyl, isopropyl, methoxy, ethoxy, propoxy or isopropoxy.

When the term "halo" is used herein, there are included chloro, fluoro, bromo and iodo. The preferred halo substituent is chloro because the other halogens offer no particular advantages over chloro and because of the relatively low cost and ease of preparation of the required chloro intermediates. However, the other above-named halo substituents are also satisfactory.

The novel compounds represented by Formulas I and II above are essentially colorless in the depicted lactone form. When the compounds of Formula I, bearing two or three indole substituents, and those of Formula II are contacted with an acidic medium, for example, silica gel or one of the types regularly employed in pressure-sensitive carbonless duplicating systems, for example, silton clay or phenolic resins, they develop a colored image of good to excellent tinctorial strength. The prompt development of color on contact with silica gel, silton clay or a phenolic resin demonstrates that these compounds are highly suitable for use as colorless precursors, that is, color-forming substances in pressure-sensitive carbonless duplicating systems. For such application, the compounds may be incorporated in any of the commercially accepted systems known in the carbonless duplicating art. A typical technique for such application is as follows. Solutions of the colorless precursor compounds in suitable aromatic solvents are microencapsulated by well-known procedures. The microcapsules are coated on the reverse side of a transfer sheet with the aid of a suitable binder and the coated transfer sheet is then assembled in a manifold with the microcapsule coated side in contact with a receiving sheet coated with an electron accepting substance, for example, silton clay or a phenolic resin. Application of pressure to the manifold such as that exerted by a stylus, typewriter or other form of writing or printing causes the capsules on the reverse side to rupture. The solution of the color former released from the ruptured microcapsules flows to the receiving sheet and on contact with the acidic medium thereon promptly forms a bluish-green to reddish-purple colored image of good tinctorial strength. It is, of course, obvious that variants of this mode of application can be utilized. For example, the receiving sheet in a manifold can alternatively be coated with the subject compounds and the acidic developing agent can be contained in microcapsules applied to the reverse side of the top sheet in the manifold.

It has also been found that when the compounds of Formulas I and II are intimately mixed with an acidic developer of the type generally employed in thermal papers, that is, papers which produce a colored image when contacted with a heated stylus or heated type, for example, bisphenol A, heating of the mixture produces a colored image of varying shades from green-blue to purple depending on the particular compound of the invention employed. The ability of the compounds of Formulas I and II to readily form a deep color when heated in admixture with an acidic developer such as bisphenol A, makes them useful in thermal paper marking systems, either where an original or a duplicate copy is prepared by contacting the thermal paper with a heated stylus or heated type in any of the methods generally known in the art.

As stated above, the compounds of Formula I are useful as color precursors, particularly in the art of carbonless duplicating systems. As with other colorless precursors currently in use in the art, the compounds are colorless under neutral or basic conditions, but become colored when contacted with an acidic material such as silica gel, a phenolic resin or an acidic clay. It is frequently desired that the images produced by such color precursors by copiable by xerographic means. A widely used color precursor is 3,3-bis(4-dimethylaminophenyl)-6-dimethylaminophthalide or, as this compound has been more simply designated, crystal violet lactone. Crystal violet lactone produces a blue image which is intense but which suffers the disadvantage of being poorly copiable by xerographic means. To counteract this disadvantage, other color precursors have been mixed with crystal violet lactone as described, for example, in U.S. Pat. No. 3,525,630. The images produced by the compounds of Formula I, which are generally equal or greater in intensity of color than images produced by crystal violet lactone, are readily copiable by xerographic means. For this reason, the difficulties inherent in using mixed color precursors to achieve xerographic copiability can be avoided by using a compound of Formula I above.

The colored images produced by development of the compounds of Formula I, either by thermal means or by contact with acidic material have been found to possess good to excellent light stability on exposure to daylight or to a daylight fluorescent lamp.

In view of the utility of the final products as described above, another aspect of this invention resides in pressure-sensitive carbonless duplicating systems and thermal paper marking systems containing as a color-forming substance any of the 3,5-bis(1-R-2-$R_1$-5/6-Y-3- indolyl)-2(3H)-furanones depicted by Formula II; the 3,5-bis(1-R-2-$R_1$-5/6-Y-3-indolyl)-5-(1-$R_2$-2-$R_3$-5/6-$Y_1$-3-indolyl)-2(5H)-furanones depicted by Formula III; the 3,5-bis(1-R-2-$R_1$-5/6-Y-3-indolyl)-2(5H)-furanones represented by Formula IV; and the 5-(1-R-2-$R_1$-5/6-Y-3-indolyl)-5-(1-$R_2$-2-$R_3$-5/6-$Y_1$-3-indolyl)-3,4-dichloro-2(5H)-furanones represented by Formula V wherein R, $R_1$, $R_2$, $R_3$, Y and $Y_1$ have the same respective meanings given in relation to Formulas II, III, IV and V.

The compounds of Formula I in which Z and $Z_1$ are both chlorine and $Z_2$ is hydrogen have also been found to produce colored images in brown to black shades when paper treated with them without an acid developer is contacted with a heated stylus or heated type. This group of compounds of the invention are decidedly advantageous over those compounds employed in thermal duplicating systems which require the incorporation of an acidic developer such as bisphenol A in that they afford thermal copy systems containing only a single component for the production of a colored image. Thus, in another of its aspects, this invention resides in a thermal paper marking system containing as a color forming substance a 5-(1-R-2-$R_1$-5/6-Y-3-indolyl)-3,4-dichloro-2(5H)-furanone having the structural formula

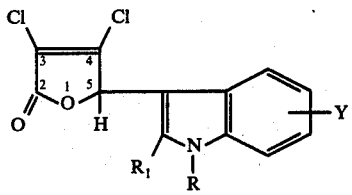

in which R is hydrogen, non-tertiary alkyl of one to eight carbon atoms, alkenyl of two to four carbon atoms, benzyl or benzyl substituted in the benzene ring by one or two of halo or alkyl of one to three carbon atoms; $R_1$ represents hydrogen, alkyl of one to three carbon atoms or phenyl; and Y represents one or two of hydrogen, alkyl of one to three carbon atoms, alkoxy of one to three carbon atoms, halo or nitro.

The best mode contemplated by the inventors of carrying out this invention will now be described so as to enable any person skilled in the art to which it pertains to make and use the same.

The compounds of Formulas I and II are prepared by a variety of processes. More specifically, the 3,5,5-tris-indolyl-substituted compounds represented by Formula III, which fall within the scope of those depicted in Formula I, are prepared by interacting approximately an equimolar quantity of the appropriate 2,4-bis(1-R-2-$R_1$-5/6-Y-3-indolyl)-4-oxobutanoic acid with the appropriate 1-$R_2$-2-$R_3$-5/6-$Y_1$-indole. The reaction is conveniently carried out in a dehydrating solvent, for example, acetic anhydride preferably in the presence of oxygen at a temperature in the range of 10° to 100° C, but more desirably, at a temperature in the range of 20° to 75° C. The 3,5-bis(1-R-2-$R_1$-5/6-Y-3-indolyl)-5-(1-$R_2$-2-$R_3$-5/6-$Y_1$-3-indolyl)-2(5H)-furanone thus obtained can be isolated if desired, either by filtration from the reaction medium or alternatively by extraction into and subsequent isolation from an aromatic organic solvent, for example, benzene or toluene. In the latter method, the reaction medium is slowly combined with a mixture of the aromatic organic solvent, water, ice and sufficient alkali, for example, ammonia or sodium hydroxide to render the mixture slightly alkaline. The organic layer is separated and dried over a suitable drying agent and then filtered. There is added to the clear solution a suitable coprecipitating inert organic solvent, for example, hexane or a petroleum ether which causes the product to be precipitated or to crystallize from the solution. The separated final product is then collected and dried by conventional means.

In a second and alternative preparative method, the 3,5,5-tris-indolyl-substituted compounds of Formula III can be conveniently obtained by interacting the appropriate 3,5-bis(1-R-2-$R_1$-5/6-Y-3-indolyl)-2(3H)-furanone of Formula II with approximately an equimolar quantity of an appropriate 1-$R_2$-2-$R_3$-5/6-$Y_1$-indole. This reaction is also carried out in a dehydrating solvent, for example, acetic anhydride preferably in the presence of oxygen and at a temperature in the range of 10° to 100° C, but more desirably, at a temperature in the range of 20° to 75° C to obtain the desired 3,5-bis(1-R-2-$R_1$-5/6-Y-3-indolyl)-5-(1-$R_2$-2-$R_3$-5/6-$Y_1$-3-indolyl)-2(5H)-furanone of Formula III. The product is isolated in a manner similar to that indicated in the process described above.

The 3,5,5-tris-indolyl-substituted compounds of Formula III in which the indole moieties are the same can be prepared by interacting maleic anhydride with approximately two molecular proportions of the appropriate 1-R-2-$R_1$-5/6-Y-indole. The reaction is conveniently carried out in a dehydrating solvent, for example, acetic anhydride preferably in the presence of oxygen at a temperature in the range of 10° to 140° C, but more desirably, at a temperature in the range of 75° C to 140° C to obtain the desired 3,5,5-tris(1-R-2-$R_1$-5/6-Y-3-indolyl)-2(5H)-furanones of Formula III. The final products are isolated in a manner similar to that indicated in the first mode of synthesis described above. Although the stoichiometry of this reaction calls for three molecular proportions of the indole for one of maleic anhydride, it has been found that more satisfactory yields and better quality of the product are obtained when an excess of maleic anhydride is present, as is the case when less than three molecular proportions are employed.

The 2(3H)-furanones of Formula II are useful as final products as well as intermediates to the 2(5H)-furanones and are conveniently prepared by the cyclization of an appropriate 2,4-bis(1-R-2-$R_1$-5/6-Y-3-indolyl)-4-oxobutanoic acid to the corresponding 3,5-bis(1-R-2-$R_1$-5/6-Y-3-indolyl)-2(3H)-furanone. The cyclization is conveniently carried out in a dehydrating solvent, for example, acetic anhydride preferably in the presence of oxygen at a temperature in the range of 10° to 50° C, but more desirably, at a temperature in the range of 20° to 30° C to obtain the desired product of Formula II. The final product is isolated by filtration.

The 3,5-bis(1-R-2-$R_1$-5/6-Y-3-indolyl)-2(5H)-furanone compounds represented by Formula IV are conveniently prepared by rearrangement of the double bond in the furanone ring of the corresponding 3,5-bis(1-R-2-$R_1$-5/6-Y-3-indolyl)-2(3H)-furanones. The reaction is effected by heating the appropriate 3,5-bis-(indolyl)-substituted-2(3H)-furanone in a dehydrating solvent, for example, acetic anhydride preferably in the presence of oxygen at a temperature in the range of 40° to 100° C, but more desirably, at a temperature in the range of 50° to 70° C to obtain the desired 3,5-bis(1-R-2-$R_1$-5/6-Y-3-indolyl)-2(5H)-furanones which are conveniently isolated by filtration.

The final products represented by Formula V, which are 5-(1-R-2-$R_1$-5/6-Y-3-indolyl)-5-(1-$R_2$-2-$R_3$-5/6-$Y_1$-3-indolyl)-3,4-dichloro-2(5H)-furanones, are conveniently prepared by interacting the appropriate 4-(1-R-2-$R_1$-5/6-Y-3-indolyl)-2,3-dichloro-4-oxo-2-butenoic acid with approximately an equimolar quantity of an appropriate 1-$R_2$-2-$R_3$-5/6-$Y_1$-indole. The reaction is conveniently carried out in a dehydrating solvent, for example, acetic anhydride preferably in the presence of oxygen at a temperature in the range of 10° to 100° C, but more desirably, at a temperature in the range of 20° to 30° C to obtain the desired 5-(1-R-2-$R_1$-5/6-Y-3-indolyl)-5-(1-$R_2$-2-$R_3$-5/6-$Y_1$-3-indolyl)-3,4-dichloro-2(5H)-furanone. These final products are isolated either by filtration from the reaction medium or by drowning the reaction mixture in a mixture of water, ice and sufficient alkali, for example, ammonia to render the drowned mixture slightly alkaline. The separated product is then collected by filtration.

The 5-(1-R-2-$R_1$-5/6-Y-3-indolyl)-3,4-dichloro-2(5H)-furanone compounds represented by Formula VI are conveniently prepared by the method described by Rees and Sabet in the Journal of the Chemical Society, 687–691 (1965) which comprises condensing commercially available mucochloric acid with an appropriate indole.

The 2,4-bis(1-R-2-$R_1$-5/6-Y-3-indolyl)-4-oxobutanoic acids, represented by Formula VII, which are required for the preparation of the final products of Formulas II, III and IV, are conveniently prepared according to the procedure of Diels and Alder, Ann. Chem. 490, 277–294 (1931), comprising the condensation of maleic anhydride with approximately two molar equivalents of an appropriate 1-R-2-$R_1$-5/6-Y-indole.

The 4-(1-R-2-$R_1$-5/6-Y-3-indolyl)-2,3-dichloro-4-oxo-2-butenoic acids represented by Formula VIII, which are required for the preparation of the final products of Formula V are conveniently prepared by interacting commercially available dichloromaleic anhydride with approximately an equimolar quantity of an appropriate 1-R-2-$R_1$-5/6-Y-indole. The reaction is carried out in an inert organic solvent, for example, ethylene dichloride at a temperature in the range of 10° to 100° C, but preferably in the temperature range of 10° to 30° C to obtain the desired 2-butenoic acids of Formula VIII which are isolated by filtration.

It has been found that in the above-described preparative procedures for obtaining the final products which involve a keto-acid, whether as a starting material per se or generated in situ, it is desirable to introduce oxygen, preferably in the form of air during the reaction. The precise role of oxygen in these reactions is not understood at this time; but it is observed that substantially improved yields of the final products obtained through the keto-acid intermediates are obtained when oxygen is present during the reaction period. Although various modes of introducing oxygen into the reaction mixtures can be employed, for example, by the use of hydrogen peroxide, it has been found that entirely satisfactory results are obtained by incorporating air into the reaction mixture. This is conveniently accomplished by any of several conventional techniques, for example, by rapid agitation of the reaction mixture, by passing a stream of air over the reaction mixture or by bubbling air into the mixture by means of a gas dispersion device.

Indole and the substituted indoles required as intermediates for the preparation of the keto-acid intermediates of Formulas VII and VIII and for the final products of Formulas I, II, III, V and VI form an old and well-known class of compounds which are readily obtained by conventional procedures well known in the art. The following compounds are exemplary of indoles useful in the practice of this invention.

Indole,
1-Methylindole,
2-Methylindole,
1,2-Dimethylindole,
1-Ethyl-2-methylindole,
2-Phenylindole,
1-Propyl-2-methylindole,
1-Benzyl-2-methylindole,
1-Butyl-2-methylindole,
1-Octyl-2-methylindole,
2-Ethyl-5-methylindole,
1-Benzyl-5-fluoroindole,
1-Methyl-6-nitroindole,
5-Methoxy-1-butylindole,
1-Allyl-2-methylindole,
1,2-Dimethyl-6-nitroindole,
1-(4-Chlorobenzyl)-2-methyl-5-nitroindole,
1-Methyl-5-bromo-6-nitroindole,
2,5,6-Trimethylindole,
1-Isobutyl-2-methylindole,
6-Bromo-2-methylindole,
1-Hexylindole,
1-(2,5-Dimethylbenzyl)-2-methylindole,
2-Propylindole,
6-Chloro-2-phenylindole,
1-(2-Ethylhexyl)-2-methylindole,
1-(2,6-Dichlorobenzyl)-2-methylindole,
1-Vinyl-2-methylindole,
2-Ethyl-6-methylindole,
6-Fluoro-1-benzylindole,
1-(4-Bromobenzyl)-2-isopropylindole,
1-(3-Chlorobenzyl)-2-ethylindole,
5-Chloro-1-benzylindole,
1-(2-Fluorobenzyl)-2-methylindole,
5-Iodo-1-(1-methylhexyl)indole,
5,6-Dimethoxyindole,
1-(2-Methylbenzyl)-2-methylindole,
5,6-Dichloro-2-phenylindole,
1-Isoamylindole, and
1-[3-(2-Methyl)-1-propenyl]-2-methylindole.

The molecular structures of the compounds of the invention were assigned on the basis of the modes of synthesis and study of their infrared, nuclear magnetic resonance and mass spectra.

The following examples will further illustrate the invention without, however, limiting it thereto. All melting points are uncorrected.

EXAMPLE 1

A. A stirred solution of 20.0 g (0.204 mole) of maleic anhydride and 70.0 g (0.408 mole) of 1-n-propyl-2-methylindole in 200 ml of benzene was heated at reflux for a period of approximately eighteen hours and then allowed to cool to ambient temperature. The solid which separated from the cooled solution was collected by filtration, washed with fresh chilled benzene and dried in vacuo at 60° C to obtain 30.0 g of 2,4-bis(1-n-propyl-2-methyl-3-indolyl)-4-oxobutanoic acid (Formula VII: R=$CH_3CH_2CH_2$; $R_1$=$CH_3$; Y=H) as a white solid melting over the range 210° to 215° C.

Infrared maxima appeared at 1695 (C=O; s) and 1638 (C=O; s) $cm^{-1}$. The nuclear magnetic resonance spectrum was in agreement with the assigned structure.

Analysis by mass spectrum showed m/e peaks at 444(M+) and at 400(M+-CO₂).

B. A stirred mixture of 7.0 g (0.0157 mole) of the 2,4-bis(1-n-propyl-2-methyl-3-indolyl)-4-oxobutanoic acid prepared as described in A above, 2.7 g (0.017 mole) of 1-ethyl-2-methylindole, 100 ml of acetic anhydride and 1.0 ml of glacial acetic acid was aerated by bubbling air through the mixture for approximately eight hours at a temperature in the range of 48°-52° C. The solid that formed was collected by filtration. A second crop of product was obtained by drowning the filtrate in a stirred mixture of ice, benzene and sufficient concentrated ammonia hydroxide to make the mixture slightly alkaline. The benzene layer was separated, dried over molecular sieves, filtered and the filtrate set aside for several hours. The crystals, which separated from the solution, were collected by filtration and combined with the first crop of product. The combined solids were dried in vacuo at 60° C to obtain 3,5-bis(1-n-propyl-2-methyl-3-indolyl)-5-(1-ethyl-2-methyl-3-indolyl)-2(5H)-furanone (Formula III: $R=CH_3CH_2CH_2$; $R_1=R_3=CH_3$; $R_2=CH_3CH_2$; $Y=$• $Y_1=H$) as a tan solid which decomposed at 179° C.

A significant infrared maximum appeared at 1745 ($C=O$; s) cm$^{-1}$. The nuclear magnetic resonance spectrum was in complete agreement with the assigned structure. Analysis by mass spectrum showed m/e peaks at 569(M+) and at 525(M+-CO₂).

A benzene solution of the product spotted on silica gel, an acidic clay or a phenolic resin develops a deep blue-colored image which has good xerographic copiability and good lightfastness.

C. Following a procedure similar to that described above in part A of this example by using 6-bromo-2-methylindole instead of 1-n-propyl-2-methylindole, there is obtained 2,4-bis(6-bromo-2-methyl-3-indolyl)-4-oxobutanoic acid (Formula VII: $R=H$; $R_1=CH_3$; $Y=6-Br$).

D. Following a procedure similar to that described above in part B of this example except that 2,4-bis(6-bromo-2-methyl-3-indolyl)-4-oxobutanoic acid is used in place of 2,4-bis(1-n-propyl-2-methyl-3-indolyl)-4-oxobutanoic acid, there is obtained 3,5-bis(6-bromo-2-methyl-3-indolyl)-5-(1-ethyl-2-methyl-3-indolyl)-2(5H)-furanone (Formula III: $R=Y_1=H$; $R_1=R_3=CH_3$; $R_2=CH_3CH_2$; $Y=6-Br$).

E. When 6-chloro-2-phenylindole is substituted for 1-n-propyl-2-methylindole in part A of this example, there is obtained 2,4-bis(6-chloro-2-phenyl-3-indolyl)-4-oxobutanoic acid (Formula VII: $R=H$; $R_1=C_6H_5$; $Y=6-Cl$).

F. Following a procedure similar to that described above in part B of this example by using 2,4-bis(6-chloro-2-phenyl-3-indolyl)-4-oxobutanoic acid instead of 2,4-bis(1-n-propyl-2-methyl-3-indolyl)-4-oxobutanoic acid, and 2-propylindole is substituted for 1-ethyl-2-methylindole, there is obtained 3,5-bis(6-chloro-2-phenyl-3-indolyl)-5-(2-propyl-3-indolyl)-2(5H)-furanone (Formula III: $R=R_2=Y_1=H$; $R_1=C_6H_5$; $R_3=CH_3CH_2CH_2$; $Y=6-Cl$).

EXAMPLE 2

A. A stirred mixture of 7.1 g (0.016 mole) of 2,4-bis(1-n-propyl-2-methyl-3-indolyl)-4-oxobutanoic acid (prepared as described in Example 1, part A), 2.8 g (0.016 mole) of 1-n-propyl-2-methyl-indole, 100 ml of acetic anhydride and 1.0 ml of glacial acetic acid was heated under an atmosphere of air at approximately 60° C for a period of approximately sixteen hours. The resultant solution was then cooled to 10° C by means of an ice bath. The solid which separated from the solution was collected by filtration and dried in vacuo at 60° C. A second crop of product was obtained by drowning the filtrate in a stirred mixture of ice, benzene and sufficient concentrated ammonium hydroxide to make the mixture slightly alkaline. The benzene layer was separated, dried over molecular sieves and filtered. Approximately three volumes of n-hexane was slowly stirred into the clear benzene solution which was then evaporated at ambient temperature in a fume hood to approximately one-half of its original volume. The crystals which separated from the solution were collected by filtration and dried in vacuo at 60° C and combined with the first crop. There was thus obtained 3,5,5-tris(1-n-propyl-2-methyl-3-indolyl)-2(5H)-furanone (Formula III: $R=R_2=CH_3CH_2CH_2$; $R_1=R_3=CH_3$; $Y=Y_1=H$) as a light tan solid which softened at 82° C and melted with decomposition at 96° C.

A significant infrared maximum appeared at 1755 ($C=O$; s) cm$^{-1}$. The nuclear magnetic resonance spectrum was in accord with the assigned structure. Analysis by mass spectrum showed m/e peaks at 597(M+) and at 553(M+-CO₂).

A benzene solution of the product spotted on silica gel, an acidic clay or a phenolic resin develops a deep blue-colored image which has good xerographic copiability and good lightfastness.

B. Following a procedure similar to that described above in part A of this example except that 2,4-bis(6-chloro-2-phenyl-3-indolyl)-4-oxobutanoic acid is used in place of 2,4-bis(1-n-propyl-2-methyl-3-indolyl)-4-oxobutanoic acid and 6-chloro-2-phenylindole is used instead of 1-n-propyl-2-methylindole, there is obtained 3,5,5-tris(6-chloro-2-phenyl-3-indolyl)-2(5H)-furanone (Formula III: $R=R_2=H$; $R_1=R_3=C_6H_5$; $Y=Y_1=6-Cl$).

EXAMPLE 3

A. A stirred mixture of 160.0 g (0.97 mole) of 1-ethyl-2-methylindole (95 percent assay), 40.0 g (0.408 mole) of maleic anhydride and 700 ml of benzene was heated at reflux for a period of approximately eighteen hours and then cooled to ambient temperature. The separated solid was collected by filtration and dried in vacuo at 60° C to obtain 52.4 g of 2,4-bis(1-ethyl-2-methyl-3-indolyl)-4-oxobutanoic acid (Formula VII: $R=CH_3CH_2$; $R_1=CH_3$; $Y=H$), a white solid melting over the range of 221°-225° C.

Upon analysis by infrared, maxima appeared at 1705 ($C=O$; s) and 1642 ($C=O$; s) cm$^{-1}$. Analysis by mass spectrum showed m/e peaks at 416(M+) and at 372(M+-CO₂).

B. A mixture of 2.9 g (0.007 mole) of 2,4-bis(1-ethyl-2-methyl-3-indolyl)-4-oxobutanoic acid prepared as described in Part A above, 4.0 g (0.0236 mole) of 1-ethyl-2-methylindole (94 percent assay) and 50 ml of acetic anhydride was stirred for approximately twenty-four hours under an atmosphere of air at ambient temperature. The separated solid was collected by filtration and dried in vacuo at 60° C to obtain as a yellow-white powder 3,5,5-tris(1-ethyl-2-methyl-3-indolyl)-2(5H)-furanone (Formula III: $R=R_2=CH_3CH_2$; $R_1=R_3=CH_3$; $Y=Y_1=H$), a white solid which melted at 231°-232° C.

Infrared spectral analysis showed a maximum at 1745 ($C=O$, s) cm$^{-1}$. The nuclear magnetic resonance spectrum was concordant with the assigned structure. Mass spectral analysis showed m/e peaks at 555($M^+$) and at 511($M^+$-$CO_2$).

A benzene solution of the product when spotted on silica gel, an acidic clay or a phenolic resin develops a dark blue-violet-colored image. The developed image has good xerographic copiability and good lightfastness.

C. When 1-(4-chlorobenzyl)-2-methyl-5-nitroindole is substituted for 1-ethyl-2-methylindole in part A of this example, there is obtained 2,4-bis[1-(4-chlorobenzyl)-2-methyl-5-nitro-3-indolyl]-4-oxobutanoic acid (Formula VII: R=4-$ClC_6H_4CH_2$; $R_1$=$CH_3$; Y=5-$NO_2$).

D. Following a procedure similar to that described above in part B of this example by using 2,4-bis[1-(4-chlorobenzyl)-2-methyl-5-nitro-3-indolyl]-4-oxobutanoic acid instead of 2,4-bis(1-ethyl-2-methyl-3-indolyl)-4-oxobutanoic acid and 1-(4-chlorobenzyl)-2-methyl-5-nitroindole is substituted for 1-ethyl-2-methylindole, there is obtained 3,5,5-tris[1-(4-chlorobenzyl)-2-methyl-5-nitro-3-indolyl]-2(5H)-furanone (Formula III: R=$R_2$=4-$ClC_6H_4CH_2$; $R_1$=$R_3$=$CH_3$; Y=$Y_1$=5-$NO_2$).

EXAMPLE 4

A. A mixture of 40.0 g (0.096 mole) of 2,4-bis(1-ethyl-2-methyl-3-indolyl)-4-oxobutanoic acid (prepared as in Example 3, part A) and 450 ml of acetic anhydride was stirred approximately seventeen hours at ambient temperature under an atmosphere of air. The solid that formed was collected by filtration and washed first with acetic anhydride and then with diethyl ether. After drying at 60° C in vacuo there was obtained 34.0 g of 3,5-bis(1-ethyl-2-methyl-3-indolyl)-2(3H)-furanone (Formula II: R=$CH_3CH_2$; $R_1$=$CH_3$; Y=H) as a white solid which melted over the range 186°-188° C with decomposition.

Infrared analysis showed maxima at 1645 (C=C; m) and 1805 (C=O; s) $cm^{-1}$. Nuclear magnetic resonance analysis was in accord with the assigned structure. Mass spectral analysis showed m/e peaks at 398($M^+$) and 354($M^+$-$CO_2$).

An acetone solution of the product spotted on silica gel, an acidic clay or a phenolic resin develops a turquoise-colored image.

B. A mixture of 5.5 g (0.0138 mole) of 3,5-bis(1-ethyl-2-methyl-3-indolyl)-2(3H)-furanone, 8.0 g (0.05 mole) of 1-ethyl-2-methylindole, 100 ml of acetic anhydride and 0.25 ml of 30 percent hydrogen peroxide was stirred approximately eighteen hours at room temperature. The solid was collected by filtration and a small sample showed an infrared maximum at 1800 $cm^{-1}$ and a smaller maximum at 1745 $cm^{-1}$. The solid and the filtrate were recombined, and stirred eighteen hours at approximately 60° C. The solid was collected by filtration and dried at 60° C in vacuo to obtain 3,5,5-tris(1-ethyl-2-methyl-3-indolyl)-2(5H)-furanone (Formula III: R=$R_2$=$CH_3CH_2$; $R_1$=$R_3$=$CH_3$; Y=$Y_1$=H) as a white solid which melted at 232°-234° C.

A significant infrared maximum appeared at 1745 (C=O; s) $cm^{-1}$. The nuclear magnetic resonance spectrum was concordant with the assigned structure. Mass spectral analysis showed m/e peaks at 555($M^+$) and 511($M^+$-$CO_2$).

When a benzene solution of the product was spotted on silica gel, an acidic clay or a phenolic resin, it developed a deep blue-colored image which has good xerographic copiability and good lightfastness.

Analysis of this product demonstrates it to be identical with that obtained in Example 3, part B above.

C. Following a procedure similar to that described above in part A of this example except that 2,4-bis(6-fluoro-1-benzyl-3-indolyl)-4-oxobutanoic acid prepared by interaction of maleic anhydride and 6-fluoro-1-benzylindole by a procedure similar to that described in Example 3, part A is used in place of 2,4-bis(1-ethyl-2-methyl-3-indolyl)-4-oxobutanoic acid, there is obtained 3,5-bis(6-fluoro-1-benzyl-3-indolyl)-2(3H)-furanone (Formula II: R=$C_6H_5CH_2$; $R_1$=H; Y=6-F).

D. When 3,5-bis(6-fluoro-1-benzyl-3-indolyl)-2(3H)-furanone is substituted for 3,5-bis(1-ethyl-2-methyl-3-indolyl)-2(3H)-furanone and 5,6-dimethoxyindole is substituted for 1-ethyl-2-methylindole in the procedure described in part B of this example, there is obtained 3,5-bis(6-fluoro-1-benzyl-3-indolyl)-5-(5,6-dimethoxy-3-indolyl)-2(5H)-furanone (Formula III: R=$C_6H_5CH_2$; $R_1$=$R_2$=$R_3$=H; Y=6-F; $Y_1$=5,6-($CH_3O)_2$).

EXAMPLE 5

A. A stirred mixture of 2.25 g (0.023 mole) of maleic anhydride, 8.0 g (0.50 mole) of 1-ethyl-2-methylindole and 2.71 g of acetic anhydride was heated at reflux in an atmosphere of air for approximately thirty minutes, then cooled slightly below the reflux temperature and an additional 2.71 g of acetic anhydride were added. The reaction mixture was heated at reflux for an additional seventy minutes in the presence of air before cooling to room temperature. A portion of the thick, tar-like reaction mixture was dissolved in benzene and treated with sufficient dilute aqueous ammonia to render the mixture slightly alkaline. The benzene layer was separated and hexane slowly added to the solution causing a blue-gray solid to separate. The solid was collected by filtration and dried at 40° C in vacuo to obtain 3,5,5-tris(1-ethyl-2-methyl-3-indolyl)-2(5H)-furanone (Formula III: R=$R_2$=$CH_3CH_2$; $R_1$=$R_3$=$CH_3$; Y=$Y_1$=H) as a pale blue-gray powder which melted over the range 232°-234° C.

Infrared spectral analysis gave a significant maxima at 1750 (C=O; s) $cm^{-1}$. The assigned structure was corroborated by a concordant nuclear magnetic resonance spectrum.

A benzene solution of the product spotted on silica gel, an acidic clay or a phenolic resin develops a deep blue-colored image which has good xerographic copiability and good lightfastness.

The product obtained in this example was found upon analysis to be identical to the products obtained in part B of Examples 3, part B and 4, part B.

B. Following a procedure similar to that described above in part A of this example by using 2-ethyl-6-methylindole instead of 1-ethyl-2-methylindole, there is obtained 3,5,5-tris(2-ethyl-6-methyl-3-indolyl)-2(5H)-furanone (Formula III: R=$R_2$=H; $R_1$=$R_3$=$CH_3CH_2$; Y=$Y_1$=6-$CH_3$).

C. Following a procedure similar to that described above in part A of this example except that 1-isoamylindole is used in place of 1-ethyl-2-methylindole, there is obtained 3,5,5-tris(1-isoamyl-3-indolyl)-2(5H)-furanone (Formula III: R=$R_2$=$(CH_3)_2CHCH_2CH_2$; $R_1$=$R_3$=Y=$Y_1$=H).

D. When 1-vinyl-2-methylindole is substituted for 1-ethyl-2-methylindole in part A of this example, there is obtained 3,5,5-tris(1-vinyl-2-methyl-3-indolyl)-2(5H)- furanone (Formula III: R=R$_2$=CH$_2$=CH; R$_1$=R$_3$=CH$_3$; Y=Y$_1$=H).

E. Following a procedure similar to that described above in part A of this example by using 1-(2-methylbenzyl)-2-methylindole instead of 1-ethyl-2-methylindole, there is obtained 3,5,5-tris[1-(2-methylbenzyl)-2-methyl-3-indolyl]-2(5H)-furanone (Formula III: R=R$_2$=2-CH$_3$-C$_6$H$_4$CH$_2$; R$_1$=R$_3$=CH$_3$; Y=Y$_1$=H).

F. Following a procedure similar to that described above in part A of this example except that 5-iodo-1-(1-methylhexyl)-indole is used in place of 1-ethyl-2-methylindole, there is obtained 3,5,5-tris[5-iodo-1-(1-methylhexyl)-3-indolyl]-2(5H)-furanone (Formula III: R=R$_2$=CH$_3$(CH$_2$)$_4$CH(CH$_3$); R$_1$=R$_3$=H; Y=Y$_1$=5-I).

EXAMPLE 6

A stirred mixture of 16.8 g (0.0403 mole) of 2,4-bis(1-ethyl-2-methyl-3-indolyl)-4-oxobutanoic acid (prepared as described in Example 3, part A), 8.0 g (0.0427 mole) of 1-n-butyl-2-methyl-indole, 400 ml of acetic anhydride and 4.0 ml of glacial acetic acid was heated at approximately 60° C for approximately eighteen hours in an atmosphere of air. The resulting solution was cooled to ambient temperature and slowly added with stirring to a mixture of ice, benzene and sufficient concentrated ammonium hydroxide to render the mixture slightly alkaline. The benzene layer was separated, dried over molecular sieves and filtered. To the dried benzene filtrate there was slowly added with stirring an equal volume of n-hexane. The solid which slowly separated was collected by filtration and dried in vacuo at 60° C to obtain 3,5-bis(1-ethyl-2-methyl-3-indolyl)-5-(1-n-butyl-2-methyl-3-indolyl)-2(5H)-furanone (Formula III: R=CH$_3$CH$_2$; R$_1$=R$_3$=CH$_3$; R$_2$=CH$_3$(CH$_2$)$_2$CH$_2$; Y=Y$_1$=H) as a tan solid which melted at 98° C with decomposition.

A significant infrared maximum appeared at 1755 (C=O; s) cm$^{-1}$. The assigned structure was corroborated by a concordant nuclear magnetic resonance spectrum. Mass spectral analysis showed m/e peaks at 555(M$^+$) and at 511(M$^+$-CO$_2$).

A benzene solution of the product applied to silica gel, an acidic clay or a phenolic resin develops a blue-colored image which has good xerographic copiability and good lightfastness.

EXAMPLE 7

A. A mixture of 20.0 g (0.048 mole) of 2,4-bis(1-ethyl-2-methyl-3-indolyl)-4-oxobutanoic acid (prepared as described in Example 3, part A) and 300 ml of acetic anhydride was stirred at room temperature (25° C) for approximately eighteen hours. The solid that formed was collected by filtration and dried in vacuo at 60° C to obtain 3,5-bis(1-ethyl-2-methyl-3-indolyl)-2(3H)-furanone (Formula II: R=CH$_3$CH$_2$; R$_1$=CH$_3$; Y=H) as a white solid melting at 186°-188° C with decomposition.

Upon infrared spectral analysis, significant maxima were found at 1645(C-C; m) and at 1805 (C=O; s) cm$^{-1}$.

B. A mixture of 6.4 g (0.016 mole) of 3,5-bis(1-ethyl-2-methyl-3-indolyl)-2(3H)-furanone prepared as described in part A directly above, 2.8 g (0.016 mole) of 1-n-propyl-2-methyl indole, 100 ml of acetic anhydride and 2.0 ml of glacial acetic acid was stirred and aerated by bubbling air through the mixture for approximately sixteen hours at ambient temperature and then at a temperature of approximately 50° C for twenty-four hours. The resulting mixture was cooled to room temperature and the solid which separated was collected by filtration and dried in vacuo at 60° C to obtain 3,5-bis(1-ethyl-2-methyl-3-indolyl)-5-(1-n-propyl-2-methyl-3-indolyl)-2(5H)-furanone (Formula III: R=CH$_3$CH$_2$; R$_1$=R$_3$=CH$_3$; R$_2$=CH$_3$CH$_2$CH$_2$; Y=Y$_1$=H) as a tan solid which melted over the range 203° to 206° with decomposition.

Infrared analysis showed a maximum at 1745 (C=O; s) cm$^{-1}$. The nuclear magnetic resonance analysis was in accord with the assigned structure. Mass spectral analysis showed m/e peaks at 569(M$^+$) and at 525(M$^+$-CO$_2$).

When a benzene solution of the product is spotted on silica gel, an acidic clay or a phenolic resin a dark blue-colored image develops. The developed image demonstrates good xerographic copiability and good lightfastness.

EXAMPLE 8

Following a procedure similar to that described in Example 3, part B, 4.2 g (0.0101 mole) of 2,4-bis(1-ethyl-2-methyl-3-indolyl)-4-oxobutanoic acid prepared as described in Example 3, part A was interacted with 1.5 g (0.0104 mole) of 1,2-dimethylindole to obtain 2.0 g of 3,5-bis(1-ethyl-2-methyl-3-indolyl)-5-(1,2-dimethyl-3-indolyl)-2(5H)-furanone (Formula III: R=CH$_3$CH$_2$; R$_1$=R$_2$=R$_3$=CH$_3$; Y=Y$_1$=H) as a white solid melting at 227°-228° C.

An infrared maximum appeared at 1750 (C=O; s) cm$^{-1}$. The nuclear magnetic resonance spectrum was concordant with the assigned structure. Mass spectral analysis gave a m/e peak at 497(M$^+$-CO$_2$).

A toluene solution of the product when spotted on silica gel, an acidic clay or a phenolic resin develops a dark blue-colored image which has good xerographic copiability and good lightfastness.

EXAMPLE 9

Following a procedure similar to that described in Example 3, part B, 4.2 g (0.0101 mole) of 2,4-bis(1-ethyl-2-methyl-3-indolyl)-4-oxobutanoic acid (prepared as described in Example 3, part A) was interacted with 1.3 g (0.010 mole) of 2-methylindole to obtain 3,5-bis(1-ethyl-2-methyl-3-indolyl)-5-(2-methyl-3-indolyl)-2(5H)-furanone (Formula III: R=CH$_3$CH$_2$; R$_1$=R$_3$=CH$_3$; R$_2$=Y=Y$_1$=H), a pale blue-colored product which melted over the range of 232°-236° C with decomposition.

A significant infrared maximum appeared at 1728 (C=O; s) cm$^{-1}$. The nuclear magnetic resonance spectrum was in complete agreement with the assigned structure. Mass spectral analysis gave m/e peaks at 527(M$^+$) and 483(M$^+$-CO$_2$).

When a benzene solution of the product was spotted on silica gel, an acidic clay or a phenolic resin it developed a dark blue-colored image which has good xerographic copiability and good lightfastness.

EXAMPLE 10

A. A stirred solution of 90.0 g (0.686 mole) of 2-methylindole, 30.0 g (0.306 mole) of maleic anhydride, 350 ml of benzene and 5.0 ml of glacial acetic acid was heated at reflux under a nitrogen atmosphere for a period of approximately sixty-five hours. The resulting slurry was cooled to approximately 60° C and the solid was collected by filtration, washed with approximately 100 ml of benzene that had been heated to approximately 60° C. After drying to a constant weight of 29.7 g in vacuo at 60° C there was obtained 2,4-bis(2-methyl-3-indolyl)-4-oxobutanoic acid (Formula VII: R=Y=H; $R_1$=CH$_3$) as a pale yellow solid which melted at 217°-218° C with decomposition.

Infrared maxima appeared at 1630 (C=O; m) and 1692 (C=O; s) cm$^{-1}$. The nuclear magnetic resonance spectrum was concordant with the assigned structure. Mass spectral analysis showed m/e peaks at 360(M$^+$) and 316(M$^+$-CO$_2$).

B. Employing a procedure similar to that described in Example 3, part B above, but interacting 2.7 g (0.0075 mole) of 2,4-bis(2-methyl-3-indolyl)-4-oxobutanoic acid and 1.3 g (0.01 mole) of 2-methylindole in place of the 2,4-bis(1-ethyl-2-methyl-3-indolyl)-4-oxobutanoic acid and 1-ethyl-2-methylindole, respectively, there was obtained 3,5,5-tris(2-methyl-3-indolyl)-2(5H)-furanone (Formula III: R=R$_2$=Y=Y$_1$=H; R$_1$=R$_3$=CH$_3$), a pale blue powder which melted at 133°-135° C with decomposition.

Significant infrared maxima appeared at 1735 (C=O; s) and 3400 (N—H; w) cm$^{-1}$. Nuclear magnetic resonance analysis were in accord with the assigned structure. The mass spectrum showed a m/e peak at 427(M$^+$-CO$_2$).

A benzene solution of the product spotted on silica gel, an acidic clay or a phenolic resin developed a deep purple-colored image which has good xerographic copiability and good lightfastness.

EXAMPLE 11

Following a procedure similar to that described in Example 3, part B, but interacting 3.6 g (0.01 mole) of 2,4-bis(2-methyl-3-indolyl)-4-oxobutanoic acid, prepared as described in Example 10, part A above and 2.0 g (0.0138 mole) of 1,2-dimethylindole, there was obtained 1.2 g of 3,5-bis(2-methyl-3-indolyl)-5-(1,2-dimethyl-3-indolyl)-2(5H)-furanone (Formula III: R=Y=Y$_1$=H; R$_1$=R$_2$=R$_3$=CH$_3$) as a faint blue-colored powder which melted in the range of 207°-227° C.

Upon analysis by infrared, maxima appeared at 1730 (C=O; s) and 3400 (N—H; w) cm$^{-1}$. The nuclear magnetic resonance spectrum was concordant with the assigned structure. Analysis by mass spectrum showed m/e peaks at 485(M$^+$) and 441(M$^+$-CO$_2$).

A benzene solution of the product when spotted on silica gel, an acidic clay or a phenolic resin develops a deep grape-colored image. The developed image has good xerographic copiability and good lightfastness.

EXAMPLE 12

Employing a procedure similar to that described in Example 3, part B above, for interacting 3.6 g (0.01 mole) of 2,4-bis(2-methyl-3-indolyl)-4-oxobutanoic acid prepared as described in Example 10, part A and 1.98 g (0.0125 mole) of 1-ethyl-2-methylindole, there was obtained 3,5-bis(2-methyl-3-indolyl)-5-(1-ethyl-2-methyl-3-indolyl)-2(5H)-furanone (Formula III: R=Y=Y$_1$=H; R$_1$=R$_3$=CH$_3$; R$_2$=CH$_3$CH$_2$) as a light brown powder which melted in the range 176°-181° C.

Significant infrared maxima appeared at 1730 (C=O; s) and 3400 (N—H; w) cm$^{-1}$. The nuclear magnetic resonance spectrum was in complete agreement with the assigned structure. Mass spectral analysis showed a m/e peak at 455(M$^+$-CO$_2$).

When a toluene solution of the product is applied to silica gel, an acidic clay or a phenolic resin, it develops a deep grape-colored image which has good xerographic copiability and good lightfastness.

EXAMPLE 13

Following a procedure similar to that described in Example 3, part B above, 3.6 g (0.01 mole) of 2,4-bis(2-methyl-3-indolyl)-4-oxobutanoic acid (described above in Example 10, part A) and 2.12 g (0.01 mole) of 2-phenylindole were interacted to obtain 0.26 g of 3,5-bis(2-methyl-3-indolyl)-5-(2-phenyl-3-indolyl)-2(5H)-furanone (Formula III: R=R$_2$=Y=Y$_1$=H; R$_1$=CH$_3$; R$_3$=C$_6$H$_5$), a pale blue-colored powder which melted in the range of 204°-215° C.

Significant infrared maxima appeared at 1710 (C=O; s) and 3400 (N—H; w) cm$^{-1}$. Nuclear magnetic resonance analysis was in accord with the assigned structure. Analysis by mass spectrum showed a m/e peak at 358(M$^+$-carbon dioxide-2-methylindolyl moiety).

A benzene solution of the product spotted on silica gel, an acidic clay or phenolic resin develops a deep blue-colored image which has good xerographic copiability and good lightfastness.

EXAMPLE 14

Following a procedure similar to that described above in Example 6, 5.5 g (0.016 mole) of 2,4-bis(2-methyl-3-indolyl)-4-oxobutanoic acid prepared as described in Example 10, part A above and 3.3 g (0.016 mole) of 1-n-octyl-2-methylindole were interacted with aeration to obtain 6.0 g of 3,5-bis(2-methyl-3-indolyl)-5-(1-n-octyl-2-methyl-3-indolyl)-2(5H)-furanone (Formula III: R=Y=Y$_1$=H; R$_1$=R$_3$=CH$_3$; R$_2$=CH$_3$(CH$_2$)$_6$CH$_2$), a pale blue powder which decomposed at 134° C.

Significant infrared maxima appeared at 1730 (C=O; s) and 3395 (N—H; w) cm$^{-1}$. Nuclear magnetic resonance analysis was in accord with the assigned structure. Analysis by mass spectrum showed a m/e peak at 539(M$^+$-CO$_2$).

When a benzene solution of the product is spotted on silica gel, an acidic clay or a phenolic resin, a deep blue-colored image develops which has good xeographic copiability and good lightfastness.

EXAMPLE 15

Proceeding in a manner similar to Example 6 above, 5.5 g (0.016 mole) of 2,4-bis(2-methyl-3-indolyl)-4-oxobutanoic acid prepared as described in Example 10, part A above and 3.0 g (0.016 mole) of 1-allyl-2-methyl indole were interacted and aerated to obtain 3,5-bis(2-methyl-3-indolyl)-5-(1-allyl-2-methyl-3-indolyl)-2(5H)-furanone (Formula III: R=Y=Y$_1$=H; R$_1$=R$_3$=CH$_3$; R$_2$= CH$_2$=CHCH$_2$) as a cream-colored solid which melted over the range of 150°-174° C with decomposition.

The infrared spectrum showed maxima at 1730 (C=O; s) and 3380 (N—H; w) cm$^{-1}$. The nuclear magnetic resonance spectrum was concordant with the assigned structure. Mass spectral analysis showed a m/e peak at 467(M$^+$-CO$_2$).

A benzene solution of the product when spotted on silica gel, an acidic clay or a phenolic resin develops a deep blue-colored image which has good xerographic copiability and good lightfastness.

EXAMPLE 16

Following a procedure similar to that described in Example 2 above, 5.5 g (0.016 mole) of 2,4-bis(2-methyl- 3-indolyl)-4-oxobutanoic acid prepared as described in Example 10, part A above and 3.6 g (0.016 mole) of 1-benzyl-2-methylindole were interacted to obtain 3,5-bis(2-methyl-3-indolyl)-5-(1-benzyl-2-methyl-3-indolyl)-2(5H)-furanone (Formula III: $R=Y=Y_1=H$; $R_1=R_3=CH_3$; $R_2=C_6H_5CH_2$) as a tan solid which melted over the range 170°–180° C with decomposition.

Infrared spectral analysis showed a maximum at 1740 ($C=O$; s) cm$^{-1}$. The nuclear magnetic resonance spectrum was concordant with the assigned structure. Mass spectral analysis showed a m/e peak at 517($M^+$-$CO_2$).

An acetone solution of the product when spotted on silica gel, an acidic clay or a phenolic resin develops a blue-colored image. The developed image exhibits good xerographic copiability.

EXAMPLE 17

Proceeding in a manner similar to that described above in Example 6, 5.5 g (0.016 mole) of 2,4-bis(2-methyl-3-indolyl)-4-oxobutanoic acid prepared as described in Example 10, part A above and 3.0 g (0.016 mole) of 1-n-butyl-2-methylindole were interacted to obtain 3,5-bis(2-methyl-3-indolyl)-5-(1-n-butyl-2-methyl-3-indolyl)-2(5H)-furanone (Formula III: $R=Y=Y_1=H$; $R_1=R_3=CH_3$; $R_2=CH_3(CH_2)_2CH_2$), a pale blue powder which melted over the range of 180°–184° C with decomposition.

A significant infrared maximum appeared at 1730 ($C=O$; s) cm$^{-1}$. The nuclear magnetic resonance spectrum corroborated the assigned structure. Mass spectral analysis showed a m/e peak at 483($M^+$-$CO_2$).

An acetone solution of the product applied to silica gel, an acidic clay or a phenolic resin develops a deep blue-colored image which has good xerographic copiability and good lightfastness.

EXAMPLE 18

A. A stirred mixture of 30.0 g (0.2 mole) of 1,2-dimethylindole, 10.0 g (0.10 mole) of maleic anhydride, 170 ml of toluene and 0.5 ml of glacial acetic acid was heated at reflux temperature for approximately seventeen hours. After cooling to ambient temperature, the solid was collected by filtration and washed on the filter with a small portion of fresh toluene. The toluene wet solid was suspended with stirring in benzene, warmed to approximately 60° C and filtered. The collected white crystals were dried at 60° C in vacuo to obtain 16.0 g of 2,4-bis(1,2-dimethyl-3-indolyl)-4-oxobutanoic acid (Formula VII: $R=R_1=CH_3$; $Y=H$) which melted over the range of 243°–245° C.

Upon infrared spectral analysis, maxima appeared at 1645 ($C=O$; m) and 1695 ($C=O$; s) cm$^{-1}$. Mass spectral analysis showed a m/e peak at 344($M^+$-$CO_2$).

B. Following a procedure similar to that described above in Example 3, part B, 3.8 g (0.02 mole) of 2,4-bis(1,2-dimethyl-3-indolyl)-4-oxobutanoic acid (prepared in part A above) and 2.0 g (0.02 mole) of 1,2-dimethylindole were interacted to obtain 1.5 g of 3,5,5-tris(1,2-dimethyl-3-indolyl)-2(5H)-furanone (Formula III: $R=R_1=R_2=R_3=CH_3$; $Y=Y_1=H$) as a white solid which melted in the range of 232° to 234° C.

A significant infrared maximum appeared at 1750 ($C=O$; s) cm$^{-1}$. The nuclear magnetic resonance spectrum was concordant with the assigned structure. Analysis by mass spectrum gave m/e peaks at 513($M^+$) and 469($M^+$-$CO_2$).

A toluene solution of the product when spotted on silica gel, an acidic clay or a phenolic resin develops a deep blue-colored image which has good xerographic copiability and good lightfastness.

EXAMPLE 19

Proceeding in a manner similar to that described above in Example 3, part B, 3.8 g (0.012 mole) of 2,4-bis(1,2-dimethyl-3-indolyl)-4-oxobutanoic acid prepared as described in Example 18, part A above and 2.0 g (0.012 mole) of 1-ethyl-2-methylindole were interacted to obtain 3,5-bis(1,2-dimethyl-3-indolyl-5-(1-ethyl-2-methyl-3-indolyl)-2(5H)-furanone (Formula III: $R=R_1=R_3=CH_3$; $R_2=CH_3CH_2$; $Y=Y_1=H$) as a pale blue-colored powder which melted over the range 191°–194° C.

A significant infrared meximum appeared at 1745 ($C=O$; s) cm$^{-1}$. The nuclear magnetic resonance spectrum was concordant with the assigned structure. Analysis by mass spectrum showed m/e peaks at 527($M^+$) and 483($M^+$-$CO_2$).

An acetone solution of the product when spotted on silica gel, an acidic clay or a phenolic resin develops a deep blue-colored image which has good xerographic copiability and good lightfastness.

EXAMPLE 20

A. Following a procedure similar to that described above in Example 1, part A, 54.0 g (0.190 mole) of 1-n-butyl-2-methylindole and 19.0 g (0.095 mole) of maleic anhydride was interacted to obtain 26.0 g of 2,4-bis(1-n-butyl-2-methyl-3-indolyl)-4-oxobutanoic acid (Formula VII: $R=CH_3(CH_2)_2CH_2$; $R_1=CH_3$; $Y=H$) as a pale blue-white solid which melted over the range of 203° to 205° C. An infrared maximum was observed at 1700 ($C=O$; s) cm$^{-1}$.

B. Proceeding in a manner similar to that described above in Example 3, part B, 7.3 g (0.016 mole) of 2,4-bis(1-n-butyl-2-methyl-3-indolyl)-4-oxobutanoic acid (prepared in part A directly above) and 2.1 g (0.016 mole) of 2-methylindole was interacted to obtain 3,5-bis(1-n-butyl-2-methyl-3-indolyl)-5-(2-methyl-3-indolyl-2(5H)-furanone (Formula III: $R=CH_3(CH_2)_2CH_2$; $R_1=R_3=CH_3$; $R_2=Y=Y_1=H$) as a pale blue-colored solid which melted over the range of 175°–180° C with decomposition.

An infrared maxima appeared at 1730 ($C=O$; s) cm$^{-1}$. Nuclear magnetic resonance analysis was in accord with the assigned structure. Analysis by mass spectrum showed a m/e peak at 539($M^+$-$CO_2$).

An acetone solution of the product spotted on silica gel, an acidic clay or a phenolic resin develops a deep blue-colored image which has good xerographic copiability and good lightfastness.

EXAMPLE 21

A mixture of 7.6 g (0.016 mole) of 2,4-bis(1-butyl-2-methyl-3-indolyl)-4-oxobutanoic acid, prepared as described in Example 20, part A above, 3.0 g (0.016 mole) of 1-n-butyl-2-methylindole, 100 g of acetic anhydride and 1.0 ml of glacial acetic acid was stirred and aerated, by bubbling air through the mixture, at approximately 60° C for a period of twenty hours. The acetic anhydride and acetic acid were removed from the mixture by distillation at reduced pressure yielding a syrup-like material which was then dissolved in benzene and treated with a sufficient quantity of dilute aqueous ammonia to render the mixture slightly alkaline. The benzene layer was separated and to it there was slowly added hexane causing a thick, tar-like substance to settle out of the solution. The tar-like material was redissolved in benzene and to the solution there was added hexane which again caused a tar-like solid to separate. After setting approximately eighteen hours in the mixed solvent system the tar-like solid gave way to a friable solid material. The product was collected by filtration and dried at 60° C in vacuo to obtain 3,5,5-tris(1-n-butyl-2-methyl-3-indolyl)-2(5H)-furanone (Formula III: R=$R_2$=$CH_3(CH_2)_2CH_2$; $R_1$=$R_3$=$CH_3$; Y=$Y_1$=H), a pale brown-colored solid which melted over the range 111° to 146° C.

A significant infrared maximum was observed at 1755 (C=O; s) $cm^{-1}$. The nuclear magnetic resonance spectrum was consistent with the assigned structure.

A benzene solution of the product spotted on silica gel, an acidic clay or a phenolic resin develops a deep blue-colored image. The developed image has good xerographic copiability and good lightfastness.

EXAMPLE 22

A. A mixture of 8.0 g (0.019 mole) of 2,4-bis(1-ethyl-2-methyl-3-indolyl)-4-oxobutanoic acid prepared as described in Example 3, part A, and 100 ml of acetic anhydride was stirred approximately seventeen hours under an atmosphere of air at ambient temperature. The solid was filtered and washed first with fresh acetic anhydride and then with diethyl ether to obtain 3,5-bis(1-ethyl-2-methyl-3-indolyl)-2(3H)-furanone (Formula II: R=$C_2H_5$; $R_1$=$CH_3$; Y=H) as a white solid which melted over the range 186°–188° C with decomposition.

A significant infrared maximum appeared at 1805 (C=O; s) $cm^{-1}$. The nuclear magnetic resonance spectrum was concordant with the assigned structure.

When a benzene solution of the product is applied to silica gel, an acidic clay or a phenolic resin, a turquoise image develops.

B. The (3H) isomer obtained in A above was converted to the (5H) isomer by the following procedure. The solid from part A above and the filtrate from part A above were combined with stirring at approximately 60° C in the presence of air for a period of approximately seventeen hours. The mixture was then cooled to room temperature and the resultant solid was collected by filtration and washed first with small portions of fresh acetic anhydride and then with diethyl ether. At this point, the infrared spectral analysis showed no shift in the value for the carbonyl band. The solid and the reaction filtrate were recombined and stirred at 75° C under an atmosphere of air for approximately fifteen hours. Upon cooling to ambient temperature, the solid was collected by filtration, washed with small portions of fresh acetic anhydride and diethyl ether and dried at 60° C in vacuo to obtain 3,5-bis(1-ethyl-2-methyl-3-indolyl)-2(5H)-furanone (Formula IV: R=$CH_3CH_2$; $R_1$=$CH_3$; Y=H) as a white solid which melted at 213°–214° C with decomposition.

A significant infrared maximum appeared at 1762 (C=O; s) $cm^{-1}$. The nuclear magnetic resonance spectrum was in complete agreement with the assigned structure. Mass spectral analysis showed m/e peaks at 398($M^+$) and 354($M^+$-$CO_2$).

An acetone solution of the product spotted on silica gel, an acidic clay or a phenolic resin develops a turquoise-colored image.

C. Following a procedure similar to that described above in part A of this example by using 2,4-bis(2,5,6-trimethyl-3-indolyl)-4-oxobutanoic acid (prepared by the interaction of maleic anhydride and 2,5,6-trimethylindole in a manner similar to that described in Example 3, part A) instead of 2,4-bis(1-ethyl-2-methyl-3-indolyl)-4-oxobutanoic acid, there is obtained 3,5-bis(2,5,6-trimethyl-3-indolyl)-2(3H)-furanone (Formula II: R=H; $R_1$=$CH_3$; Y=5,6-$(CH_3)_2$).

D. When 3,5-bis(2,5,6-trimethyl-3-indolyl)-2(3H)-furanone is substituted for 3,5-bis(1-ethyl-2-methyl-3-indolyl)-2(3H)-furanone in part B of this example, there is obtained 3,5-bis(2,5,6-trimethyl-3-indolyl)-2(5H)-furanone (Formula IV: R=H; $R_1$=$CH_3$; Y=5,6-$(CH_3)_2$).

E. Following a procedure similar to that described above in part A of this example except that 2,4-bis[1-(4-bromobenzyl)-2-isopropyl-3-indolyl]-4-oxobutanoic acid (prepared by the interaction of maleic anhydride and 1-(4-bromobenzyl)-2-isopropylindole in a similar manner to that described in Example 3, part A) is used in place of 2,4-bis(1-ethyl-2-methyl-3-indolyl)-4-oxobutanoic acid, there is obtained 3,5-bis[1-(4-bromobenzyl)-2-isopropyl-3-indolyl]-2(3H)-furanone (Formula II: R=4-$BrC_6H_4CH_2$; $R_1$=$(CH_3)_2CH$; Y=H).

F. Substituting 3,5-bis[1-(4-bromobenzyl)-2-isopropyl-3-indolyl]-2(3H)-furanone for 3,5L -bis(1-ethyl-2-methyl-3-indolyl)-2(3H)-furanone in the procedure described in part B above in this example, there is obtained 3,5-bis[1-(4-bromobenzyl)-2-isopropyl-3-indolyl]-2(5H)-furanone (Formula IV: R=4-$BrC_6H_4CH_2$; $R_1$=$(CH_3)_2CH$; Y=H).

EXAMPLE 23

A. Proceeding in a manner similar to that described above in Example 4, part A, 8.0 g (0.02 mole) of 2,4-bis(1,2-dimethyl-3-indolyl)-4-oxobutanoic acid prepared as described in Example 18, part A above was interacted with 100 ml of acetic anhydride to obtain 3,5-bis(1,2-dimethyl-3-indolyl)-2-(3H)-furanone (Formula II: R=$R_1$=$CH_3$; Y=H) as a white solid.

The significant infrared maxima were at 1645 (C=C; m) and 1785 (C=O; s) $cm^{-1}$.

An acetone solution of the product when spotted on silica gel, an acidic clay or a phenolic resin develops a turquoise color.

B. The (3H) isomer obtained in A above was converted to the (5H) isomer by the following procedure. The solid and filtrate from part A of this example were recombined and stirred at approximately 60° C for a period of approximately seventeen hours in the presence of air, and then at approximately 75° C for a period of approximately fifteen hours. The solid in the mixture was collected by filtration, washed with a small portion of fresh acetic anhydride and dried at 60° C in vacuo to obtain 3,5-bis(1,2-dimethyl-3-indolyl)-2-(5H)-furanone (Formula IV: R=$R_1$=$CH_3$; Y=$Y_1$=H) as a tan solid which melted over the range of 238°–241° C with decomposition.

Infrared spectral analysis showed a maximum at 1762 (C=O; s) $cm^{-1}$. The nuclear magnetic resonance spectrum was concordant with the assigned structure.

An acetone solution of the product when spotted on silica gel, an acidic clay or a phenolic resin develops a turquoise-colored image.

C. Following a procedure similar to that described above in part A of this example by using 2,4-bis{1-[3-(2-methyl)-1-propenyl]-2-methyl-3-indolyl}-4-oxobutanoic acid (prepared by interacting maleic anhydride and 1-[3-(2-methyl)-1-propenyl]-2-methylindole in a manner similar to that described in Example 18, part A) instead of 2,4-bis(1,2-dimethyl-3-indolyl)-4-oxobutanoic acid, there is obtained 3,5-bis{1-[3-(2-methyl)-1-propenyl]-2-methyl-3-indolyl}-2(3H)-furanone (Formula II: $R=CH_2=CH(CH_3)CH_2$; $R_1=CH_3$; $Y=H$).

D. Following a procedure similar to that described above in part B of this example except that 3,5-bis{1-[3-(2-methyl)-1-propenyl]-2-methyl-3-indolyl}-2(3H)-furanone is used in place of 3,5-bis(1,2-dimethyl-3-indolyl)-2-(3H)-furanone, there is obtained 3,5-bis{1-[3-(2-methyl)-1-propenyl]-2-methyl-3-indolyl}-2(5H)-furanone (Formula IV: $R=CH_2=CH(CH_3)CH_2$; $R_1=CH_3$; $Y=H$).

E. When 3,5-bis(6-fluoro-1-benzyl-3-indolyl)-2(3H)-furanone is substituted for 3,5-bis(1,2-dimethyl-3-indolyl)-2(3H)-furanone in part B of this example, there is obtained 3,5-bis-(6-fluoro-1-benzyl-3-indolyl)-2(5H)-furanone (Formula IV: $R=C_6H_5CH_2$; $R_1=H$; $Y=6-F$).

F. Following a procedure similar to that described above in part A of this example by using 2,4-bis(6-chloro-2-phenyl-3-indolyl)-4-oxabutanoic acid instead of 2,4-bis(1,2-dimethyl-3-indolyl)-4-oxobutanoic acid, there is obtained 3,5-bis(6-chloro-2-phenyl-3-indolyl)-2(3H)-furanone (Formula II: $R=H$; $R_1=C_6H_5$; $Y=6-Cl$).

G. Following a procedure similar to that described above in part B of this example except that 3,5-bis(6-chloro-2-phenyl-3-indolyl)-2(3H)-furanone is used in place of 3,5-bis(1,2-dimethyl-3-indolyl-2(3H)-furanone, there is obtained 3,5-bis (6 chloro-2-phenyl-3-indolyl)-2(5H)-furanone (Formula IV: $R=H$; $R_1=C_6H_5$; $Y=6-Cl$).

When 2,4-bis(1-n-butyl-5-methoxy-3-indolyl)-4-oxobutanoic acid (prepared by interacting 1-n-butyl-5-methoxyindole and maleic anhydride in a manner similar to that described in Example 18, part A) is substituted for 2,4-bis(1,2-dimethyl-3-indolyl)-4-oxobutanoic acid in part A of this example, there is obtained 3,5-bis(1-n-butyl-5-methoxy-3-indolyl)-2(3H)-furanone (Formula II: $R=CH_3(CH_2)_2CH_2$; $R_1=H$, $Y=5-CH_3O$).

I. Following a procedure similar to that described above in part B of this example by using 3,5-bis(1-n-butyl-5-methoxy-3-indolyl)-2(3H)-furanone instead of 3,5-bis(1,2-dimethyl-3-indolyl)-2-(3H)-furanone, there is obtained 3,5-bis(1-n-butyl-5-methoxy-3-indolyl)-2-(5H)-furanone (Formula IV: $R=CH_3(CH_2)_2CH_2$; $R_1=H$; $Y=5-CH_3O$).

EXAMPLE 24

A. A mixture of 10.0 g (0.07 mole) of 1,2-dimethylindole, 12.0 g (0.07 mole) of dichloromaleic anhydride and 200 ml of ethylene dichloride was stirred at ambient temperature for approximately eighteen hours. The solid present in the reaction mixture was collected by filtration. After drying at 60° C in vacuo there was obtained 20.0 g of 4-(1,2-dimethyl-3-indolyl)-2,3-dichloro-4-oxo-2-butenoic acid (Formula VIII: $R=R_1=CH_3$; $Y=H$) as a pale blue solid which melted over the range 150° to 153° C. Infrared spectral analysis showed a maximum at 1712 (C=O; s) $cm^{-1}$.

B. A mixture of 2.5 g (0.017 mole) of 1,2-dimethylindole, 5.3 g (0.017 mole) of 4-(1,2-dimethyl-3-indolyl)-2,3-dichloro-4-oxo-2-butenoic acid prepared as described in part A directly above and 130 ml of acetic anhydride were stirred at ambient temperature under an atmosphere of air for approximately thirty-five hours. An additional 1.0 g (0.0069 mole) of 1,2-dimethylindole was added and stirring was continued for an additional seventeen hours. The solid was collected from the reaction mixture by filtration and dried at 60° C in vacuo. There was thus obtained 5.0 g of 5,5-bis(1,2-dimethyl-3-indolyl)-3,4-dichloro-2(5H)-furanone (Formula V: $R=R_1=R_2=R_3=CH_3$; $Y=Y_1=H$), a pale purple-colored solid which did not melt up to a temperature of 300° C.

Significant infrared maxima appeared at 1628 (C=C; m) and 1762 (C=O; s) $cm^{-1}$. The nuclear magnetic resonance spectrum was in complete agreement with the assigned structure. Mass spectral analysis showed a m/e peak at 358($M^+-CO_2-HCl$).

A toluene solution of the product spotted on silica gel, an acidic clay or a phenolic resin develops a grape-colored image which possesses excellent xerographic copiability.

C. Following a procedure similar to that described above in part A of this example by using 2-ethyl-5-methylindole instead of 1,2-dimethylindole, there is obtained 4-(2-ethyl-5-methyl-3-indolyl)-2,3-dichloro-4-oxo-2-butenoic acid (Formula VIII: $R=H$; $R_1=CH_3CH_2$; $Y=5-CH_3$).

D. Following a procedure similar to that described above in part B of this example except that 4-(2-ethyl-5-methyl-3-indolyl)-2,3-dichloro-4-oxo-2-butenoic acid is used in place of 4-(1,2-dimethyl-3-indolyl)-2,3-dichloro-4-oxo-2-butenoic acid and 1-benzyl-5-fluoroindole is substituted for 1,2-dimethylindole, there is obtained 5-(2-ethyl-5-methyl-3-indolyl)-5-(1-benzyl-5-fluoro-3-indolyl)-3,4-dichloro-2(5H)-furanone (Formula V: $R=R_3=H$; $R_1=CH_3CH_2$; $R_2=C_6H_5CH_2$; $Y=5-CH_3$; $Y_1=5-F$).

E. When 1-benzyl-5-fluoroindole is substituted for 1,2-dimethylindole in part A of this example, there is obtained 4-(1-benzyl-5-fluoro-3-indolyl)-2,3-dichloro-4-oxo-2-butenoic acid (Formula VIII: $R=C_6H_5CH_2$; $R_1=H$; $Y=5-F$).

F. Following a procedure similar to that described above in part B of this example by using 4-(1-benzyl-5-fluoro-3-indolyl)-2,3-dichloro-4-oxo-2-butenoic acid instead of 4-(1,2-dimethyl-3-indolyl)-2,3-dichloro-4-oxo-2-butenoic acid and 1-methyl-6-nitroindole in place of 1,2-dimethylindole, there is obtained 5-(1-benzyl-5-fluoro-3-indolyl)-5-(1-methyl-6-nitro-3-indolyl)-3,4-dichloro-2(5H)-furanone (Formula V: $R=C_6H_5CH_2$; $R_1=R_3=H$; $R_2=CH_3$; $Y=6-F$; $Y_1=6-NO_2$).

EXAMPLE 25

A. Following a procedure similar to that described above in Example 24, part A, 26.8 g (0.16 mole) of dichloromaleic anhydride and 25.6 g (0.16 mole) of 1-ethyl-2-methyl indole were interacted to obtain 40.0 g of 4-(1-ethyl-2-methyl-3-indolyl)-2,3-dichloro-4-oxo-2-butenoic acid (Formula VIII: $R=CH_3CH_2$; $R_1=CH_3$; $Y=H$) as a red-blue solid.

Significant infrared maxima appeared at 1725 (C=O, s), 1595 (C=O; m) and 1585 (C=C; w) $cm^{-1}$. The nuclear magnetic resonance spectrum was consistant with the assigned structure. Analysis by mass spectrum showed m/e peaks at 325($M^+$) and 289 ($M^+-HCl$).

B. A mixture of 10.0 g (0.047 mole) of 4-(1-ethyl-2-methyl-3-indolyl)-2,3-dichloro-4-oxo-2-butenoic acid, 4.0 g (0.030 mole) of 2-methylindole and 150 ml of acetic anhydride was stirred at ambient temperature in an atmosphere of air for approximately seventeen hours and the solid which formed was collected by filtration. After drying in vacuo at 60° C there was obtained 5-(1- ethyl-2-methyl-3-indolyl)-5-(2-methyl-3-indolyl)-3,4-dichloro-2(5H)-furanone (Formula V: R=CH$_3$CH$_2$; R$_1$=R$_3$=CH$_3$; R$_2$=Y=Y$_1$=H) as a blue-colored solid which melted over the range of 282°-285° C.

Significant infrared maxima appeared at 1623 (C=C; m), 1762 (C=O; s) and 3400 (N—H; w) cm$^{-1}$. Nuclear magnetic resonance analysis was in accord with the assigned structure. Analysis by mass spectrum showed m/e peaks at 394(M$^+$-CO$_2$) and 359(M$^+$-CO$_2$-Cl).

When a benzene solution of the product is spotted on silica gel, an acidic clay or a phenolic resin, it develops a grape-colored image which has excellent xerographic copiability.

C. Following a procedure similar to that described above in part A of this example by using 1-allyl-2-methylindole instead of 1-ethyl-2-methylindole, there is obtained 4-(1-allyl-2-methyl-3-indolyl)-2,3-dichloro-4-oxo-2-butenoic acid (Formula VIII: R=CH$_2$=CHCH$_2$; R$_1$=CH$_3$; Y=H).

D. Following a procedure similar to that described above in part B of this example except that 4-(1-allyl-2-methyl-3-indolyl)-2,3-dichloro-4-oxo-2-butenoic acid is used in place of 4-(1-ethyl-2-methyl-3-indolyl)-2,3-dichloro-4-oxo-2-butenoic acid and 1-n-hexylindole is substituted for 2-methylindole, there is obtained 5-(1-allyl-2-methyl-3-indolyl)-5-(1-n-hexyl-3-indolyl)-3,4-dichloro-2(5H)-furanone (Formula V: R=CH$_2$=CHCH$_2$; R$_1$=CH$_3$; R$_2$=CH$_3$(CH$_2$)$_4$CH$_2$; R$_3$=Y=Y$_1$=H).

E. When 5-methoxy-1-n-butylindole is substituted for 1-ethyl-2-methylindole in part A of this example, there is obtained 4-(1-n-butyl-5-methoxy-3-indolyl)-2,3-dichloro-4-oxo-2-butenoic acid (Formula VIII: R=CH$_3$(CH$_2$)$_2$CH$_2$; R$_1$=H; Y=5-CH$_3$O).

F. Following a procedure similar to that described above in part B of this example by using 4-(1-n-butyl-5-methoxy-3-indolyl)-2,3-dichloro-4-oxo-2-butenoic acid instead of 4-(1-ethyl-2-methyl-3-indolyl)-2,3-dichloro-4-oxo-2-butenoic acid and 1-(3-chlorobenzyl)-2-ethylindole is substituted for 2-methylindole, there is obtained 5-(1-n-butyl-5-methoxy-3-indolyl)-5-[1-(3-chlorobenzyl)-2-ethyl-3-indolyl]-3,4-dichloro-2(5H)-furanone (Formula V: R=CH$_3$(CH$_2$)$_2$CH$_2$; R$_1$=Y$_1$=H; R$_2$=3-ClC$_6$H$_4$CH$_2$; R$_3$=CH$_3$CH$_2$; Y=5-CH$_3$O).

EXAMPLE 26

A. Proceeding in a manner similar to that described above in Example 24, Part A, 6.5 g (0.05 mole) of 2-methylindole and 8.4 g (0.05 mole) of dichloromaleic anhydride were interacted to obtain 4-(2-methyl-3-indolyl)-2,3-dichloro-4-oxo-2-butenoic acid (Formula VIII: R=Y=H; R$_1$=CH$_3$) as a green-colored solid.

B. Following a procedure similar to that described above in Example 25, part B, 5.0 g (0.017 mole) of 4-(2-methyl-3-indolyl)-2,3-dichloro-4-oxo-2-butenoic acid and 2.7 g (0.017 mole) of 1-ethyl-2-methylindole were interacted to obtain 5-(2-methyl-3-indolyl)-5-(1-ethyl-2-methyl-3-indolyl)-2,3-dichloro-2(5H)-furanone (Formula V: R=Y=Y$_1$=H; R$_1$=R$_3$=CH$_3$; R$_2$=CH$_3$CH$_2$) as a red-blue solid which melted in the range of 282°-285° C.

Upon analysis by infrared, maxima appeared at 1762 (C=O; s) and 3400 (N-H; w) cm$^{-1}$. The nuclear magnetic resonance spectrum was concordant with the assigned structure. Analysis by mass spectrum showed m/e peaks at 394(M$^+$-CO$_2$) and 359(M$^+$-CO$_2$-Cl).

A benzene solution of the product when spotted on silica gel, an acidic clay or a phenolic resin develops a deep purple-colored image which has excellent xerographic copiability.

EXAMPLE 27

A. A mixture of 10.0 g (0.052 mole) of 2-phenylindole, 8.8 g (0.052 mole) of dichloromaleic anhydride and 150 ml of ethylene dichloride was stirred at ambient temperature for approximately 48 hours. The solid that formed was collected by filtration and dried at 60° C in vacuo to obtain 4-(2-phenyl-3-indolyl)-2,3-dichloro-4-oxo-2-butenoic acid (Formula VIII: R=Y=H; R$_1$=C$_6$H$_5$) as a tan-colored solid which melted over the range 150°-152° C.

Infrared spectral analysis showed a maximum at 1705 (C=O; s) cm$^{-1}$. The nuclear magnetic resonance spectrum was consistent with the assigned structure.

B. A mixture of 7.0 g (0.02 mole) of 4-(2-phenyl-3-indolyl)-2,3-dichloro-4-oxo-2-butenoic acid (prepared in part A above), 3.5 g (0.02 mole of 1-ethyl-2-methylindole and 200 ml of acetic anhydride was stirred at ambient temperature in an atmosphere of air for approximately seventeen hours. The pale blue solid that formed was collected by filtration and dried in vacuo at 60° C to obtain 5-(2-phenyl-3-indolyl)-5-(1-ethyl-2-methyl-3-indolyl)-3,4-dichloro-2(5H)-furanone (Formula V: R=Y=Y$_1$=H; R$_1$=C$_6$H$_5$; R$_2$=CH$_3$CH$_2$; R$_3$=CH$_3$) as a tan-colored solid which started to sinter at 213° C and was completely melted at 225° C.

Significant infrared maxima appeared at 1764 (C=O; s) and 3380 (N-H; w) cm$^{-1}$. The nuclear magnetic resonance spectrum was in complete agreement with the assigned structure. Mass spectral analysis showed a m/e peak at 441(M$^+$-CO$_2$).

A benzene solution of the product spotted on silica gel, an acidic clay or a phenolic resin develops a deep blue-colored image which has excellent xerographic copiability.

EXAMPLE 28

A stirred mixture of 2.0 g (0.006 mole) of 4-(1-ethyl-2-methyl-3-indolyl)-2,3-dichloro-4-oxo-2-butenoic acid prepared as described above in Example 25, part A, 1.0 g (0.006 mole) of 1-ethyl-2-methylindole and 50 ml of acetic anhydride was warmed to 60° C to obtain a green-colored solution. The solution was stirred for approximately eighteen hours at ambient temperature under an atmosphere of air. The resulting blue solution was slowly added to a mixture of ice and sufficient concentrated ammonium hydroxide to render the mixture slightly alkaline. A solid which slowly separated from the solution was collected by filtration and slurried in toluene at room temperature. The powder-like solid was collected by filtration and dried at 60° C in vacuo. There was thus obtained 5,5-bis(1-ethyl-2-methyl-3-indolyl)-3,4-dichloro-2(5H)-furanone (Formula V: R=R$_2$=CH$_3$CH$_2$; R$_1$=R$_3$=CH$_3$; Y=Y$_1$=H) as a pale blue solid which decomposed at 157° C.

A significant infrared maximum appeared at 1760 (C=O; s) cm$^{-1}$. Nuclear magnetic resonance analysis was in accord with the assigned structure. Analysis by mass spectrum showed m/e peaks at 466(M$^+$) and 422(M$^+$-CO$_2$).

An acetone solution of the product spotted on silica gel, an acidic clay or a phenolic resin develops a deep purple-colored image which has excellent xerographic copiability.

EXAMPLE 29

A stirred mixture of 20.3 g (0.12 mole) of mucochloric acid, 14.1 g (0.12 mole) of indole and 125 ml of benzene was heated for approximately twenty hours at reflux temperature. The reaction mixture was cooled to ambient temperature and a dark brown solid which had separated was collected by filtration. This solid was purified by two successive recrystallizations from benzene at approximately 60° C, with the aid of decolorizing charcoal. After the second recrystallization, the purified product was dried at 60° C in vacuo to obtain 5.3 g of the known 5-(3-indolyl)-3,4-dichloro-2(5H)-furanone (Formula VI: $R=R_1=Y=H$), a pale green-colored solid, which first melted at 174° C, then turned black and finally decomposed at 182° C.

Significant infrared maxima appeared at 1629 ($C=C$; s), 1745 ($C=O$; s) and 3335 (N-H; s) cm$^{-1}$. The nuclear magnetic resonance spectrum was in complete agreement with the assigned structure. Mass spectral analysis showed a m/e peak at 267(M$^+$).

An intimately ground mixture of 0.05 g of the product obtained directly above and 0.05 g of Bisphenol A, was slowly heated in a test tube. A color change from white to red was observed as the mixture melted over the range 138°–150° C with decomposition.

Proceeding in a manner similar to that described in Example 29, the following 5-(1-R-2-$R_1$-5/6-Y-3-indolyl)-3,4-dichloro-2(5H)-furanones of Formula VI above were prepared by interaction of mucochloric acid and the appropriate indole.

EXAMPLE 30

5-(2-methyl-3-indolyl)-3,4-dichloro-2-(5H)-furanone (Formula VI: $R=Y=H$; $R_1=CH_3$), a white solid melting over the range of 175° to 185° C with decomposition, in intimate admixture with an equal weight of Bisphenol A thermally develops to a deep blue color at 160° C.

EXAMPLE 31

5-(1-ethyl-2-methyl-3-indolyl)-3,4-dichloro-2(5H)-furanone (Formula VI: R-$C_2H_5$; $R_1=CH_3$; $Y=H$) was obtained as a white solid melting at 122.5°–124° C and thermally develops to a deep blue color at 125° C when heated in intimate admixture with an equal weight of Bisphenol A.

EXAMPLE 32

5-(1-n-butyl-2-methyl-3-indolyl)-3,4-dichloro-2(5H)-furanone (Formula VI: $R=CH_3(CH_2)_2CH_2$; $R_1=CH_3$; $Y=H$) was obtained as a white solid melting at 87°–89° C. This compound thermally develops to a deep blue color when an intimate mixture of the compound and an equal weight of Bisphenol A are heated at 140° C.

EXAMPLE 33

5-(1-n-octyl-2-methyl-3-indolyl)-3,4-dichloro-2(5H)-furanone (Formula VI: $R=CH_3(CH_2)_6CH_2$; $R_1=CH_3$; $Y=H$), a white solid melting at 83°–84.5° C, thermally developed to a deep blue color at 140° C when heated in intimate admixture with an equal weight of Bisphenol A.

EXAMPLE 34

5-(1-allyl-2-methyl-3-indolyl)-3,4-dichloro-2(5H)-furanone (Formula VI: $R=CH_2=CHCH_2$; $R_1=CH_3$; $Y=H$) was obtained as a gray solid which melts at 108°–110° C with decomposition. This compound thermally developed to a purple-black color at 125° C when heated in intimate admixture with an equal weight of Bisphenol A.

EXAMPLE 35

5-(1-benzyl-2-methyl-3-indolyl)-3,4-dichloro-2(5H)-furanone (Formula VI: $R=CH_2C_6H_5$; $R_1=CH_3$; $Y=H$), a white solid melting at 144°–148° C with decomposition, thermally developed to a purple-black color at 140° C when heated in intimate admixture with an equal weight of Bisphenol A.

The infrared analysis, nuclear magnetic resonance analyses and mass spectral analyses obtained for the products of Examples 30 to 35, inclusive were concordant for the assigned structures given in those examples.

EXAMPLE 36

Following a procedure similar to that described above in Example 29 by using 2-ethyl-5-methylindole instead of indole, there is obtained 5-(2-ethyl-5-methyl-3-indolyl)-3,4-dichloro-2(5H)-furanone (Formula VI: $R=H$; $R_1=CH_3CH_2$; $Y=$5-$CH_3$).

EXAMPLE 37

Following a procedure similar to that described above in Example 29 except that 1-methyl-5-bromo-6-nitroindole is used in place of indole, there is obtained 5-(1-methyl-5-bromo-6-nitro-3-indolyl)-3,4-dichloro-2(5H)-furanone (Formula VI: $R=CH_3$; $R_1=H$; $Y=$5-Br-6-$NO_2$).

EXAMPLE 38

When 6-chloro-2-phenylindole is substituted for indole in Example 29 hereinabove, there is obtained 5-(2-phenyl-6-chloro-3-indolyl)-3,4-dichloro-2(5H)-furanone (Formula VI: $R=H$; $R_1=C_6H_5$; $Y=$6-Cl).

EXAMPLE 39

Following a procedure similar to that described above in Example 29 by using 5-iodo-1-(1-methylhexyl)indole instead of indole, there is obtained 5-[5-iodo-1-(1-methylhexyl)-3-indolyl]-3,4-dichloro-2(5H)-furanone (Formula VI: $R=CH_3(CH_2)_4CH(CH_3)$; $R_1=H$; $Y=$5-I).

EXAMPLE 40

Following a procedure similar to that described above in Example 29 except that 1-(4-bromobenzyl)-2-isopropylindole is used in placed of indole, there is obtained 5-[1-(4-bromobenzyl)-2-isopropyl-3-indolyl]-3,4-dichloro-2(5H)-furanone (Formula VI: $R=$4-Br$C_6H_4CH_2$; $R_1=(CH_3)_2CH$; $Y=H$).

EXAMPLE 41

The use of the compounds of Formulas II through V and described in Examples 1 through 28 as color forming components in pressure sensitive microencapsulated copying systems is illustrated with reference to the product of Example 7.

A. A mixture of 196 ml of distilled water and 15.0 g of pigskin gelatin was stirred at approximately 50° C for approximately 45 minutes. There was then added to the mixture a warmed (approximately 50° C) solution of 49.0 g of alkylated biphenyls and 1.0 g of 3,5-bis(1-ethyl-2-methyl-3-indolyl)-5-(1-n-propyl-2-methyl-3-indolyl)-2(5H)-furanone (Formula III: $R=CH_3CH_2$; $R_1=R_3=CH_3$; $R_2=CH_3CH_2CH_2$; $Y=Y_1=H$), prepared as described above in Example 7. The resulting solution was stirred for approximately fifteen minutes. A second solution of 81.0 ml of distilled water and 10.0 g of gum arabic was then prepared and warmed to approximately 50° C for approximately one hour.

B. The two solutions, the first containing water, gelatin, alkylated biphenyls and the product, and the second containing water and gum arabic were mixed and the pH adjusted to 9 by the addition of approximately 0.7 ml of 20 percent aqueous sodium hydroxide. The resulting mixture was transferred to a larger reactor equipped with a variable speed one-half horsepower Eppenbach Homo-Mixer (Gifford-Wood Co., Hudson, N.Y.) and there was added over a period of two to three minutes 650 ml of distilled water which had been heated to 50° C. With the stirrer running at an applied voltage of between 20 to 25 volts there was slowly added sufficient ten percent aqueous acetic acid to set the pH at 4.5, this being the point where coacervation was initiated. The stirrer speed was increased by raising the applied voltage to approximately thirty volts and approximately four drops of 2-ethylhexanol were added to suppress foaming. After approximately twenty minutes, a sample of the suspension was examined microscopically and found to have stabilized in the range of 20 to 25 microns particle size whereupon an external ice/water bath was immediately placed around the reactor containing the suspension. At approximately 20° C, the agitation speed was reduced by decreasing the applied voltage to the range of 20 to 25 volts. Cooling was continued and at approximately 15° C, 10.0 ml of glutaraldehyde was added over a period of five minutes. When the internal temperature reached 10° C, the agitation speed was further reduced by lowering the applied voltage to approximately 20 volts and these conditions maintained for approximately thirty minutes. At this time, the Eppenbach Homo-Mixer was replaced with a conventional blade type laboratory agitator and the suspension was stirred an additional three hours during which period the temperature was allowed to warm to room temperature. The microencapsulated product was isolated by pouring the slurry through an ASTM 18 stainless steel sieve to remove any large agglomerates and then collecting the capsules by filtration. The collected capsules were washed successively with four 100 ml portions of distilled water each and stored as a water wet pulp. A sample of the pulp analyzed by drying in vacuo at 80° C was found to consist of 37.5 percent solids.

C. To 125 ml of distilled water, 10.6 g of oxidized corn starch was added over a period of ten to fifteen minutes with stirring. This mixture was heated to a temperature in the range of 70°-80° C and maintained until all the starch dissolved. The starch solution was cooled to ambient temperature and there was added 100 g of the capsule-containing water wet pulp from part B above and 43.0 ml of distilled water. The capsules and starch solution were mixed at room temperature using an Eppenbach Homo-Mixer set at an applied voltage of 25 volts for five minutes and then at an applied voltage of 30 volts for an additional five minutes to complete the suspension of the capsules in the starch solution.

D. The stock starch-microcapsule suspension prepared in part C above was coated on paper sheets to a thickness of approximately 0.0015 inch and the coated paper air dried. The paper thus coated with the microencapsulated colorless precursor was assembled as the top sheet in a manifold system by positioning the coated side in contact with the coated side of a commercially available receiving sheet coated with a color developer of the electron accepting type. More specifically, papers coated with a phenolic resin and with an acidic clay were employed in this test. An image was then drawn with a stylus on the top sheet bearing the microencapsulated colorless precursor on its reverse side causing the affected microcapsules to rupture thus allowing the solution of the colorless precursor held by said microcapsules to flow into contact with the color developing substance on the receiving sheet whereupon a deep blue-colored image promptly formed. The developed image exhibited good lightfastness when exposed to daylight or to a daylight fluorescent lamp for extended periods.

When evaluated in a duplicating system prepared and tested as described above, the product of Example 3B, 3,5,5-tris(1-ethyl-2-methyl-3-indolyl)-2(5H)-furanone, produced a blue-colored developed image; the product of Example 6, 2,5-bis(1-ethyl-2-methyl-3-indolyl)-5-(1-n-butyl-2-methyl-3-indolyl)-2(5H)-furanone, produced a blue-colored developed image; the product of Example 20B, 3,5-bis(1-n-butyl-2-methyl-3-indolyl)-5-(2-methyl-3-indolyl)-2(5H)-furanone, produced a blue-colored developed image; and the product of Example 28, 5,5-bis(1-ethyl-2-methyl-3-indolyl)-3,4-dichloro-2(5H)-furanone, produced a purple-colored developed image.

EXAMPLE 42

The utility of the furanones of Formulas I and II whose preparations are described in the foregoing examples as color forming components in thermal marking systems is illustrated by the incorporation and testing of the compound of Example 28, 5,5-bis(1-ethyl-2-methyl-3-indolyl)-2,3-dichloro-2(5H)-furanone in a thermal sensitive marking paper. The test paper was prepared by a procedure similar to that described in U.S. Pat. No. 3,539,375.

A. A mixture of 20 g of 5,5-bis(1-ethyl-2-methyl-3-indolyl)-3,4-dichloro-2(5H)-furanone, 8.6 g of a ten percent aqueous solution of polyvinyl alcohol (approximately 99 percent hydrolyzed), 3.7 g of water and 31.6 g of 1/16 inch diameter zirconium grinding beads was charged into a container which was placed in a mechanical shaker. Shaking was effected for one hour. The zirconium beads were then removed by straining the mixture through a No. 40 sieve.

B. Similarly, a mixture of 9.8 g of 4,4'-isopropylidine diphenol (Bisphenol A), 42.0 g of a ten percent aqueous polyvinyl alcohol solution (approximately 99 percent hydrolyzed), 18.2 g of water and 221.2 g of 1/16 inch diameter zirconium grinding beads was charged into a container which was placed in a mechanical shaker. After shaking was effected for one hour, the zirconium beads were removed by straining through a No. 40 sieve.

C. A coating composition was prepared by mixing 2.1 g of the slurry from A and 47.9 g of the slurry from B. The mixture was then uniformly coated on sheets of paper at thicknesses of approximately 0.003 inch and the coated sheets air-dried. The coated paper was tested by tracing a design on the coated side of the paper on a smooth flat surface with a stylus heated to approximately 140° C. A deep brownblack image corresponding to the traced design promptly developed.

When evaluated in thermal marking paper prepared and tested as described above, the product of Example 4B, 3,5,5-tris(1-ethyl-2-methyl-3-indolyl)-2(5H)-furanone, produced a deep blue image; the product of Example 22B, 3,5-bis-(1-ethyl-2-methyl-3-indolyl)-2(5H)-furanone, produced a yellow-green image; the product of Example 31, 5-(1-ethyl-2-methyl-3-indolyl)-3,4-dichloro-2(5H)-furanone, produced a yellow-brown image; and the product of Example 22A, 3,5-bis(1-ethyl-2-methyl-3-indolyl)-2(3H)-furanone, produced a green-blue image.

EXAMPLE 43

A. Proceeding in a manner similar to that described in Example 42 above, 2.0 g of the compound of Example 31, 5-(1-ethyl-2-methyl-3-indolyl)-3,4-dichloro-2(5H)-furanone was ground in a mixture of 8.6 g of a ten percent aqueous solution of polyvinyl alcohol and 3.7 g of water.

B. A mixture of 47.9 g of ten percent aqueous polyvinyl alcohol, 22.1 g of water and 221.2 g of 1/16 inch diameter zirconium grinding beads was charged to a container and placed in a mechanical shaker. Shaking was effected for one hour and thhe zirconium beads were separated from the solution by screening through a No. 40 sieve.

C. A coating composition consisting of 2.1 g of the slurry from part A above and 47.9 g of the slurry from part B above was prepared and coated on paper sheets to a thickness of approximately 0.003 inch and the coated sheets were air-dried. The coated paper was tested by tracing a design on the coated side of the paper placed on a smooth flat surface with a stylus heated to approximately 200° C. A greenish-brown image corresponding to the traced design promptly developed.

What is claimed is:

1. A 3,5-bis(1-R-2-R$_1$-5/6-Y-3-indolyl)-5-(1-R$_2$-2-R$_3$-5/6-Y$_1$-3-indolyl)-2(5H)-furanone having the formula

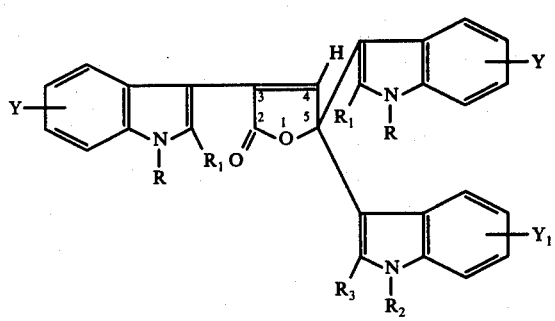

wherein:
R and R$_2$ represent hydrogen, non-tertiary alkyl of one to eight carbon atoms, alkenyl of two to four carbon atoms, benzyl or benzyl substituted in the benzene ring by one or two of halo or alkyl of one to three carbon atoms;
R$_1$ and R$_3$ represent hydrogen, alkyl of one to three carbon atoms or phenyl; and
Y and Y$_1$ represent one or two of hydrogen, alkyl of one to three carbon atoms, alkoxy of one to three carbon atoms, halo or nitro.

2. 3,5-Bis(1-n-propyl-2-methyl-3-indolyl)-5-(1-ethyl-2-methyl-3-indolyl)-2(5H)-furanone according to claim 1.

3. 3,5,5-Tris(1-n-propyl-2-methyl-3-indolyl)-2(5H)-furanone according to claim 1.

4. 3,5,5-Tris(1-ethyl-2-methyl-3-indolyl)-2(5H)-furanone according to claim 1.

5. 3,5-Bis(1-ethyl-2-methyl-3-indolyl)-5-(1-n-butyl-2-methyl-3-indolyl)-2(5H)-furanone according to claim 1.

6. 3,5-Bis(1-ethyl-2-methyl-3-indolyl)-5-(1-n-propyl-2-methyl-3-indolyl)-2(5H)-furanone according to claim 1.

7. 3,5-Bis(1-ethyl-2-methyl-3-indolyl)-5-(1,2-dimethyl-3-indolyl)-2(5H)-furanone according to claim 1.

8. 3,5-Bis(1-ethyl-2-methyl-3-indolyl)-5-(2-methyl-3-indolyl)-2(5H)-furanone according to claim 1.

9. 3,5,5-Tris(2-methyl-3-indolyl)-2(5H)-furanone according to claim 1.

10. 3,5-Bis(2-methyl-3-indolyl)-5-(1,2-dimethyl-3-indolyl)-2(5H)-furanone according to claim 1.

11. 3,5-Bis(2-methyl-3-indolyl)-5-(1-ethyl-2-methyl-3-indolyl)-2(5H)-furanone according to claim 1.

12. 3,5-Bis(2-methyl-3-indolyl)-5-(2-phenyl-3-indolyl)-2(5H)-furanone according to claim 1.

13. 3,5-Bis(2-methyl-3-indolyl)-5-(1-n-octyl-2-methyl-3-indolyl)-2(5H)-furanone according to claim 1.

14. 3,5-Bis(2-methyl-3-indolyl)-5-(1-allyl-2-methyl-3-indolyl)-2(5H)-furanone according to claim 1.

15. 3,5-Bis(2-methyl-3-indolyl)-5-(1-benzyl-2-methyl-3-indolyl)-2(5H)-furanone according to claim 1.

16. 3,5-Bis(2-methyl-3-indolyl)-5-(1-n-butyl-2-methyl-3-indolyl)-2(5H)-furanone according to claim 1.

17. 3,5,5-Tris(1,2-dimethyl-3-indolyl)-2(5H)-furanone according to claim 1.

18. 3,5-Bis(1,2-dimethyl-3-indolyl)-5-(1-ethyl-2methyl-3-indolyl)-2(5H)-furanone according to claim 1.

19. 3,5-Bis(1-n-butyl-2-methyl-3-indolyl)-5-(2-methyl-3-indolyl)-2(5H)-furanone accordng to claim 1.

20. 3,5,5-Tris(1-n-butyl-2-methyl-3-indolyl)-2(5H)-furanone according to claim 1.

* * * * *